(12) United States Patent
St Amant et al.

(10) Patent No.: US 11,259,729 B2
(45) Date of Patent: Mar. 1, 2022

(54) SYSTEMS, DEVICES, AND/OR PROCESSES FOR BEHAVIORAL AND/OR BIOLOGICAL STATE PROCESSING

(71) Applicant: ARM Ltd., Cambridge (GB)

(72) Inventors: Renee Marie St Amant, Austin, TX (US); Christopher Daniel Emmons, Austin, TX (US)

(73) Assignee: Arm Ltd., Cambridge (GB)

( * ) Notice: Subject to any disclaimer, the term of this patent is extended or adjusted under 35 U.S.C. 154(b) by 107 days.

(21) Appl. No.: 15/922,687

(22) Filed: Mar. 15, 2018

(65) Prior Publication Data

US 2019/0282155 A1    Sep. 19, 2019

(51) Int. Cl.
*A61B 5/16* (2006.01)
*G06N 20/00* (2019.01)
*G16H 20/70* (2018.01)

(52) U.S. Cl.
CPC ............. *A61B 5/167* (2013.01); *A61B 5/165* (2013.01); *G06N 20/00* (2019.01); *G16H 20/70* (2018.01)

(58) Field of Classification Search
CPC ........ A61B 5/165; A61B 5/167; G06N 20/00; G16H 20/70
See application file for complete search history.

(56) References Cited

U.S. PATENT DOCUMENTS

| | | |
|---|---|---|
| 9,704,209 B2 | 7/2017 | Proud |
| 9,997,082 B2 | 6/2018 | Kaleal |
| 2004/0133453 A1 | 7/2004 | Jomini et al. |
| 2009/0312998 A1 | 12/2009 | Berckmans |
| 2010/0003653 A1 | 1/2010 | Brown |
| 2011/0256520 A1 | 10/2011 | Siefert |
| 2014/0218187 A1 | 8/2014 | Chun et al. |
| 2014/0306821 A1 | 10/2014 | Rahman |
| 2016/0086500 A1* | 3/2016 | Kaleal, III ......... G06Q 10/0639 434/257 |
| 2016/0224803 A1* | 8/2016 | Frank ................ G06F 16/24578 |
| 2016/0270717 A1 | 9/2016 | Luna |
| 2017/0018008 A1 | 1/2017 | Hajiyev et al. |
| 2017/0200449 A1* | 7/2017 | Penilla ................. G10L 15/063 |
| 2017/0202509 A1 | 7/2017 | Sanderson |
| 2017/0368936 A1 | 12/2017 | Kojima |
| 2018/0000405 A1* | 1/2018 | Penders ............ A61B 5/14539 |
| 2018/0075490 A1* | 3/2018 | Chintalapoodi .... G06Q 30/0261 |
| 2018/0101579 A1* | 4/2018 | Jaiswal ................... G06F 9/451 |
| 2018/0218123 A1 | 8/2018 | Gomez Sanchez |
| 2019/0065970 A1* | 2/2019 | Bonutti ................. G08B 21/02 |

FOREIGN PATENT DOCUMENTS

CN    203438860 U    2/2014

OTHER PUBLICATIONS

ETHzürich Wearable devices, Screenshots of youtube video, www.youtube.com/watch?v=Qi34rm0gSZA, retrieved Nov. 28, 2018, 15 pages.

(Continued)

*Primary Examiner* — Kenny A Cese
(74) *Attorney, Agent, or Firm* — Berkeley Law & Technology Group, LLP

(57) ABSTRACT

Subject matter disclosed herein may relate to systems, devices, and/or processes for processing signals and/or states representative of behavioral and/or biological state.

18 Claims, 9 Drawing Sheets

(56) References Cited

OTHER PUBLICATIONS

U.S. Appl. No. 15/922,644, filed Mar. 15, 2018, 108 pages.
U.S. Appl. No. 15/922,644, filed Apr. 12, 2018, 3 pages.
U.S. Appl. No. 15/922,644: Non-Final Rejection, dated Sep. 25, 2018, 15 pages.
U.S. Appl. No. 15/922,644: Amendment/Req. Reconsideration—After Non-Final Reject, dated Dec. 21, 2018, 19 pages.
U.S. Appl. No. 15/922,644: Notice of Allowance and Fees Due, dated Jan. 31, 2019, 8 pages.
U.S. Appl. No. 15/922,644: Issue Fee Payment, dated Apr. 30, 2019, 11 pages.
U.S. Appl. No. 15/922,644: Response to Amendment under Rule 312, dated May 20, 2019, 3 pages.
U.S. Appl. No. 15/922,671, filed Mar. 15, 2018, 109 pages.
U.S. Appl. No. 15/922,671, filed Apr. 12, 2018, 3 pages.
Notice of Non-Compliant IDS dated May 16, 2019, U.S. Appl. No. 15/922,644, 1 pg.
Petition to Withdraw from Issue, RCE and Quickpath IDS filed Jun. 21, 2019, U.S. Appl. No. 15/922,644, 15 pgs.
Corrected Notice of Allowability dated Jun. 26, 2019, U.S. Appl. No. 15/922,644, 5 pgs.
Issue Notification dated Jun. 12, 2019, U.S. Appl. No. 15/922,644, 1 pg.
Invitation to Pay Additional Fees and, Where Applicable, Protest Fee dated Jun. 18, 2019, International Application No. PCT/GB2019/050691 4 pgs.
Communication Relating to the Results of the Partial International Search dated Jun. 18, 2019, International Application No. PCT/GB2019/050691 11 pgs.
Notification Concerning Transmittal of International Preliminary Report on Patentability dated Sep. 24, 2020, International Application No. PCT/GB2019/050691, 1 pg.
International Preliminary Report on Patentability dated Sep. 24, 2020, International Application No. PCT/GB2019/050691, 1 pg.
Written Opinion of the Internatonal Searching Authority dated Sep. 24, 2020, International Application No. PCT/GB2019/050691, 11 pgs.
Office Action, U.S. Appl. No. 15/922,671, dated Nov. 27, 2020, 55 pages.
Response to Office Action, U.S. Appl. No. 15/922,671, filed Mar. 1, 2021, 44 pages.
Final Office Action, U.S. Appl. No. 15/922,671, dated Jul. 2, 2021, 56 Pages.
Response to Final Office Action, U.S. Appl. No. 15/922,671, filed Sep. 2, 2021, 33 Pages.
Advisory Action, U.S. Appl. No. 15/922,671, dated Sep. 21, 2021, 7 Pages.
RCE/Amendment, U.S. Appl. No. 15/922,671, filed Oct. 4, 2021, 37 Pages.

* cited by examiner

SYSTEMS, DEVICES, AND/OR PROCESSES FOR BEHAVIORAL AND/OR BIOLOGICAL STATE PROCESSING

RELATED APPLICATIONS

This patent application is related to U.S. Ser. No. 15/922,644, now U.S. Pat. No. 10,373,466 entitled Systems, Devices, and/or Processes for Tracking Behavioral and/or Biological State and U.S. Ser. No. 15/922,671 entitled Systems, Devices, and/or Processes for Behavioral Content Processing, all filed concurrently with this patent application, and all hereby incorporated by reference in their entirety.

BACKGROUND

Field

Subject matter disclosed herein may relate to systems, devices, and/or processes for processing signals and/or states representative of behavioral and/or biological state.

Information

Integrated circuit devices, such as processors, for example, may be found in a wide range of electronic device types. For example, one or more processors may be used in mobile devices, such as cellular phones, for example, as well as in computers, digital cameras, tablet devices, personal digital assistants, wearable devices, etc. Mobile devices and/or other computing devices, for example, may include integrated circuit devices, such as processors, to process signals and/or states representative of a diverse of content types for a variety of purposes. With an abundance of diverse content being accessible, signal and/or state processing techniques continue to evolve. At times, however, processing signals and/or states representative of diverse content may prove to be relatively resource-demanding, which may present a number of challenges including, for example, increased processing time, storage demands, complexity, cost, and/or the like.

BRIEF DESCRIPTION OF THE DRAWINGS

Claimed subject matter is particularly pointed out and distinctly claimed in the concluding portion of the specification. However, both as to organization and/or method of operation, together with objects, features, and/or advantages thereof, it may best be understood by reference to the following detailed description if read with the accompanying drawings in which:

Figure 1:
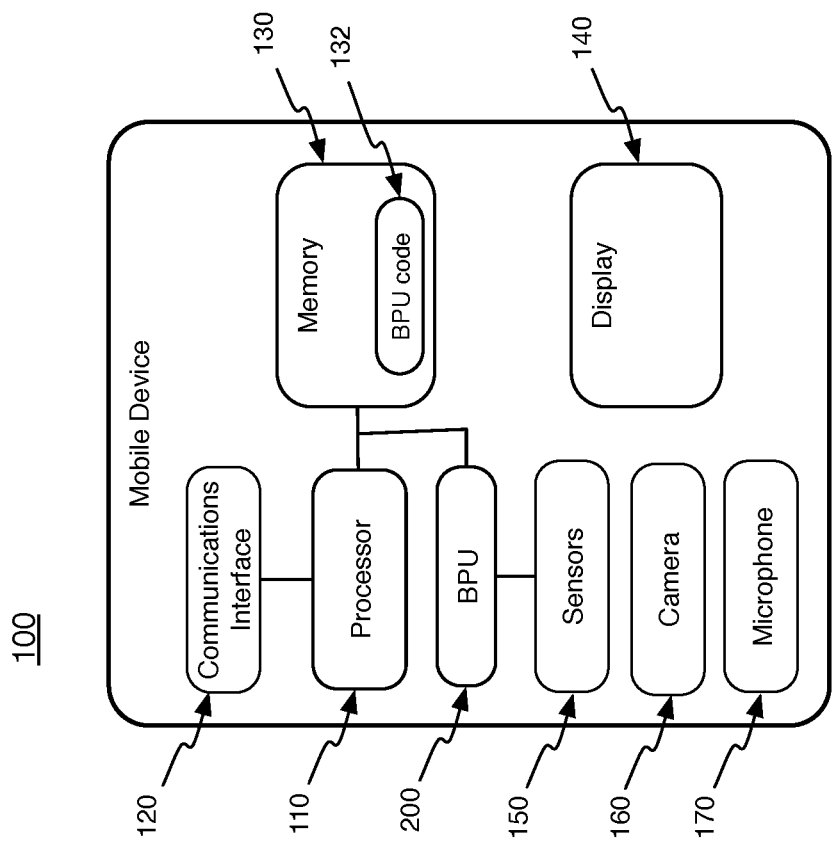
FIG. 1 is an illustration of an example mobile device, in accordance with an embodiment.

Reference is made in the following detailed description to accompanying drawings, which form a part hereof, wherein like numerals may designate like parts throughout that are corresponding and/or analogous. It will be appreciated that the figures have not necessarily been drawn to scale, such as for simplicity and/or clarity of illustration. For example, dimensions of some aspects may be exaggerated relative to others. Further, it is to be understood that other embodiments may be utilized. Furthermore, structural and/or other changes may be made without departing from claimed subject matter.

References throughout this specification to "claimed subject matter" refer to subject matter intended to be covered by one or more claims, or any portion thereof, and are not necessarily intended to refer to a complete claim set, to a particular combination of claim sets (e.g., method claims, apparatus claims, etc.), or to a particular claim. It should also be noted that directions and/or references, for example, such as up, down, top, bottom, and so on, may be used to facilitate discussion of drawings and are not intended to restrict application of claimed subject matter. Therefore, the following detailed description is not to be taken to limit claimed subject matter and/or equivalents.

DETAILED DESCRIPTION

References throughout this specification to one implementation, an implementation, one embodiment, an embodiment, and/or the like means that a particular feature, structure, characteristic, and/or the like described in relation to a particular implementation and/or embodiment is included in at least one implementation and/or embodiment of claimed subject matter. Thus, appearances of such phrases, for example, in various places throughout this specification are not necessarily intended to refer to the same implementation and/or embodiment or to any one particular implementation and/or embodiment. Furthermore, it is to be understood that particular features, structures, characteristics, and/or the like described are capable of being combined in various ways in one or more implementations and/or embodiments and, therefore, are within intended claim scope. In general, of course, as has always been the case for the specification of a patent application, these and other issues have a potential to vary in a particular context of usage. In other words, throughout the patent application, particular context of description and/or usage provides helpful guidance regarding reasonable inferences to be drawn; however, likewise, "in this context" in general without further qualification refers to the context of the present patent application.

As mentioned, integrated circuit devices, such as processors, for example, may be found in a wide range of electronic device types. For example, one or more processors may be used in mobile devices, such as cellular phones, for example, as well as in computers, digital cameras, tablet devices, personal digital assistants, wearable devices, etc. Mobile devices and/or other computing devices, for example, may include integrated circuit devices, such as processors, to process signals and/or states representative of a diverse of content types for a variety of purposes. With an abundance of diverse content being accessible, signal and/or state processing techniques continue to evolve. At times, however, processing signals and/or states representative of diverse content may prove to be relatively resource-demanding, which may present a number of challenges including, for example, increased processing time, storage demands, complexity, cost, and/or the like.

In an embodiment, content, such as behavioral profile content for a particular user, may be processed to generate recommendations, for example, with respect to a particular user. For example, content obtained at least in part via one or more sensors may be processed to generate behavioral profile content for a particular user, and/or behavioral profile content may be utilized, at least in part, to generate recommendations for a particular user directed to the particular user's current and/or future behavioral and/or biological state. Also, in an embodiment, behavioral profile content may be processed to detect "silent likes." "Silent like" and/or the like refers to at least partially non-explicit indication of approval, enjoyment, etc. of content consumed by a particular user. For example, one or more sensors may detect one or more behaviors and/or biological aspects of a particular user (e.g., head bobbing, pupil dilation indicating dopamine release, etc.) that may be understood to indicate approval, enjoyment, etc. of content being consumed by the particular user.

In another embodiment, behavioral profile content for a particular user may be processed to generate and/or select customized content for consumption by a particular user. In other embodiments, behavioral profile content may be processed at least in part to track performance changes with respect to a particular user, to improve gamer wellness, and/or to provide collaborative mental health management, as discussed more fully below. Additional embodiments may include partitioning of responsibilities in technology-assisted tasks between an operator and a computing device based, at least in part, on behavioral profile content for the operator. Of course, these are merely examples of how behavioral profile content may be processed and/or otherwise utilized, and subject matter is not limited in scope in these respects.

In an embodiment, content obtained from one or more sensors may be processed by particular hardware circuitry to generate behavioral profile content representative of a particular operator's physical, mental, and/or emotional state. For example, a processor, such as a behavioral processing unit, may be dedicated, at least in part, to processing sensor content to generate behavioral profile content representative of a particular operator's physical, mental, and/or emotional state. A processor, such as a behavioral processing unit, may include particular circuitry directed to performing particular operations to relatively more efficiently process sensor content to generate behavioral profile content for a particular operator, in an embodiment. For example, in an embodiment, a processor, such as a behavioral processing unit, may include machine learning acceleration circuitry directed to performing particular operations that may relatively more efficiently operate on sets of parameters, such as multi-dimensional sets of parameters, that may be utilized in various machine learning techniques such as, for example, neural networks, as discussed more fully below. In an embodiment, a processor, such as a behavioral processing unit, may comprise a co-processor, for example, that may operate in cooperation with a general-purpose processor, although claimed subject matter is not limited in this respect.

The terms "operator" and/or "user" refers to human individuals, and/or may be utilized herein interchangeably. In an embodiment, an operator and/or user may operate a machine, although subject matter is not limited in scope in these respects. Further, as utilized herein, "machine" refers to an article of manufacture, such as, for example, a mechanically, electrically, and/or electronically operated device for performing a task. In some embodiments, operation of a machine may be performed by a combination of an operator and/or a computing device, and/or operation of a machine may be based at least in part on a behavioral profile of at least one particular operator, as explained more fully herein.

As utilized herein, "behavioral profile content" and/or the like refers to one or more parameters representative of a current behavioral state or biological state, or a combination thereof, for at least one particular operator. Thus, for example, "behavioral profile content" and/or the like is not limited to merely behavioral aspects of a particular operator's current state, but may also include parameters representative of one or more biological aspects with respect to a particular operator, as explained more fully herein. Further, although some embodiments herein may be described in connection with "an" operator and/or "a" particular operator, subject matter is not limited to a single operator. For example, at least some embodiments may include behavioral profile content for one or more operators, although, again, claimed subject matter is not limited in scope in these respects.

Further, as utilized herein, the term "current" and/or the like refers to substantially and/or approximately current with respect to a point in time. For example, a "current" behavioral and/or biological state of a particular operator refers to a behavioral and/or biological state for the particular operator derived at least in part from relatively recent sensor content. For example, in an embodiment, behavioral profile content for a particular operator may be representative of a behavioral and/or biological state of the particular operator derived at least in part from sensor content obtained from one or more sensors within fractions of a second of being generated.

FIG. 1 is an illustration of an embodiment 100 of an example mobile device. In an embodiment, a mobile device, such as 100, may comprise one or more processors, such as processor 110 and/or behavioral processing unit (BPU) 200, and/or may comprise one or more communications interfaces, such as communications interface 120. In an embodiment, one or more communications interfaces, such as communications interface 120, may enable wireless communications between a mobile device, such as mobile device 100, and one or more other computing devices. In an embodiment, wireless communications may occur substantially in accordance any of a wide range of communication protocols, such as those mentioned herein, for example.

In an embodiment, a mobile device, such as mobile device 100, may include a memory, such as memory 130. In an embodiment, memory 130 may comprise a non-volatile memory, for example. Further, in an embodiment, a memory, such as memory 130, may have stored therein executable instructions, such as for one or more operating systems, communications protocols, and/or applications, for example. A memory, such as 130, may further store particular instructions, such as BPU code 132, executable by a behavioral processing unit, such as 200, to generate, at least in part, behavioral profile content. Further, in an embodiment, a mobile device, such as mobile device 100, may comprise a display, such as display 140, one or more sensors, such as one or more sensors 150, one or more cameras, such as one or more cameras 160, and/or one or more microphones, such as microphone 170, for example.

Although BPU 200 is described as executing instructions, such as BPU code 132, other embodiments of behavioral processing units may not fetch and execute code. In an embodiment, a behavioral processing unit may include dedicated and/or specialized circuitry for processing sensor content and/or for generating behavioral profile content, as described more fully below.

As utilized herein, "sensors" and/or the like refer to a device and/or component that may respond to physical stimulus, such as, for example, heat, light, sound pressure, magnetism, particular motions, etc., and/or that may generate one or more signals and/or states in response to physical stimulus. Thus, although camera 160 and/or microphone 170 are depicted in FIG. 1 as separate from sensors 150, the term "sensor" and/or the like may include microphones and/or cameras, in an embodiment. Example sensors may include, but are not limited to, one or more accelerometers, gyroscopes, thermometers, magnetometers, barometers, light sensors, proximity sensors, hear-rate monitors, perspiration sensors, hydration sensors, breath sensors, etc., and/or any combination thereof. In an embodiment, one or more sensors may monitor one or more aspects of a particular operator's biological and/or behavioral state.

In an embodiment, to generate behavioral profile content for a particular operator, a computing device, such as mobile device 100, may obtain signals and/or states representative of content from one or more sensors, such as one or more of sensors 150, camera 160, and/or microphone 170, or any combination thereof. Also, in an embodiment, a processor, such as behavioral processing unit 200, may process sensor content, such as content from one or more of sensors 150, camera 160, and/or microphone 170, or any combination thereof, to generate behavioral profile content for a particular operator. In an embodiment, a processor, such as behavioral processing unit 200, may include behavioral content processing circuitry. For example, a processor, such as behavioral processing unit 200, may include machine learning acceleration circuitry, in an embodiment.

For example, a processor, such as behavioral processing unit 200, may include one or more arithmetic units directed to operations involving relatively larger parameter sets, such as parameter sets that may be employed in machine learning, such as neural networks. In an embodiment, machine learning acceleration circuitry, such as arithmetic units directed to operations involving neural network parameter sets and/or other relatively larger parameter sets, may be utilized to process sensor content to generate behavioral profile content for a particular operator. In an embodiment, behavioral profile content may be utilized to affect operation of a particular machine, to generate recommendations for a particular operator directed to the particular operator's behavioral and/or biological state, to generate customized content for consumption by the particular operator, etc., to name but a few non-limiting examples.

In an embodiment, a general-purpose processor, such as processor 110, and a behavioral processing unit, such as 200, may comprise separate integrated circuit devices. In other embodiments, a general-purpose processor, such as processor 110, and a behavioral processing unit, such as 200, may be formed on the same integrated circuit die and/or integrated circuit package. Further, in an embodiment, a processor, such as behavioral processing unit 200, may comprise a co-processor that may operate in cooperation with a general purpose processor, such as 110. For example, a processor, such as 110, may execute code comprising operating systems, applications, etc. Also, in an embodiment, a behavioral processing unit, such as 200, may perform operations dedicated to generating behavioral profile content for one or more operators. For example, a behavioral processing unit, such as 200, may include circuitry for relatively more efficiently executing particular instructions and/or instructions sets, such as code 132, for operating on relatively larger parameters sets, such as may be utilized in connection with particular machine learning techniques, including, for example, neural networks.

In an embodiment, behavioral profile content, such as may be generated by a behavioral processing unit, such as 200, may be communicated between a behavioral processing unit, such as 200, as any of a wide range of devices, systems, and/or processes. For example, behavioral profile content generated by behavioral processing unit 200 may be stored in a memory, such as 130, and/or may be pushed and/or otherwise made available to processor 110 and/or to other devices and/or systems. In an embodiment, behavioral profile content may be communicated via one or more wired and/or wireless communication networks between a computing device, such as mobile device 100, and one or more other network devices, such as one or more other computing devices. Of course, subject matter is not limited in scope in these respects.

In an embodiment, behavioral profile content may include a particular specified set of parameters representative of a particular operator's behavioral and/or biological state that may be utilized, at least in part, by any of a wide range of devices, systems, and/or processes for any of a wide range of applications and/or purposes. In an embodiment, by generating a specified set of parameters comprising behavioral profile content, other devices, systems, applications, and/or processes, for example, may be relieved of responsibility for generating behavioral profile content and may, instead, concentrate on particular areas of expertise and/or specialization. For example, application developers may design applications to take advantage of one or more parameters of behavioral profile content for one or more particular operators without having to incur the costs (time, money, resources, etc.) of developing circuitry, code, etc. for gathering and/or processing sensor content and/or for generating behavioral profile content.

Although FIG. 1 depicts an embodiment of a mobile device, such as mobile device 100, other embodiments may include other types of computing devices. Example types of computing devices may include, for example, any of a wide range of digital electronic devices, including, but not limited to, desktop and/or notebook computers, high-definition televisions, digital video players and/or recorders, game consoles, satellite television receivers, cellular telephones, tablet devices, wearable devices, personal digital assistants, mobile audio and/or video playback and/or recording devices, or any combination of the foregoing.

Figure 2:
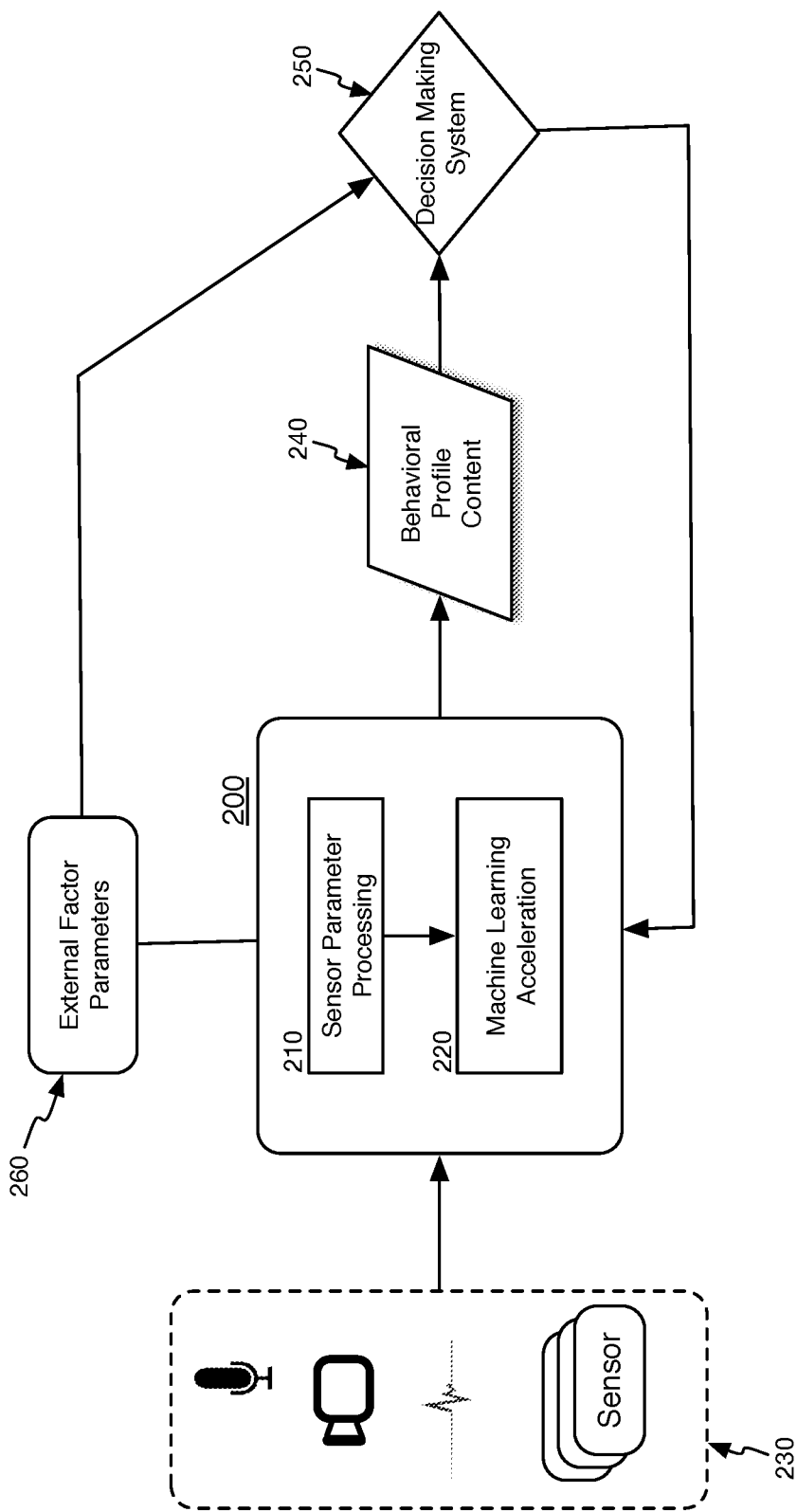
FIG. 2 is an illustration of an example processor for processing signals and/or states representative of behavioral content in a computing device, in accordance with an embodiment.

FIG. 2 is an illustration of an embodiment 200 of an processor, such as a behavioral processing unit, to process signals and/or states representative of behavioral content in a computing device. In an embodiment, to generate behavioral profile content, such as behavioral profile content 240, for a particular user, a processor, such as behavioral processing unit 200, may obtain signals and/or states representative of content from one or more sensors, such as one or more of sensors 230. Also, in an embodiment, a processor, such as behavioral processing unit 200, may process sensor content, such as content from one or more of sensors 230, to generate behavioral profile content, such as behavioral profile content 240, for a particular user. In an embodiment, a processor, such as behavioral processing unit 200, may include behavioral content processing circuitry. For example, a processor, such as behavioral processing unit 200, may include sensor parameter processing circuitry, such as circuitry 210, and/or may include machine learning acceleration circuitry, such as circuitry 220, in an embodiment.

In an embodiment, a processor, such as behavioral processing unit 200, may provide circuitry to generate, at least in part, behavioral profile content, such as behavioral profile content 240, for a particular user to be utilized for any of a wide range of possible applications, such as example applications described herein. For example, in an embodiment, behavioral profile content may be provided to a decision-making device, process, and/or system, such as decision-making device, system, and/or process 250. In an embodiment, a processor, such as behavioral processing unit 200, may relatively more efficiently process signals and/or states obtained from one or more behavioral, biological, and/or environmental sensors, or a combination thereof, associated with a particular user and/or a particular environment, for example. In an embodiment, a processor, such as behavioral processing unit 200, may calculate probabilities for "hidden" (e.g., emotional) states of a particular operator at least in part by generating behavioral profile content, such as behavioral profile content 240, that may be utilized by one or more devices, systems, and/or processes, such as decision-making device, system, and/or process 250, for any of a wide range of possible purposes. For example, as mentioned, behavioral profile content may be utilized to generate recommendations for a particular user directed to the particular user's behavioral and/or biological state, to detect silent likes, to generate customized content for consumption by the particular user, to track performance changes with respect to a particular user, to improve gamer wellness, and/or to provide collaborative mental health management, etc., to name but a few non-limiting examples. Other examples may include determining a partition of responsibility between an operator and a machine (e.g., tech-assisted driving, flying, drone operation, etc.) in situations of shared responsibility. For example, a weapon may disallow firing if an operator is determined to be angry. Also, for example, a car may disallow rapid acceleration if a driver is determined to be angry, and/or may increase its influence on steering if a driver is determined to be fatigued. Of course, subject matter is not limited in scope in these respects.

In an embodiment, machine-based decision-making, such as decision-making device, system, and/or process 250, based at least in part on behavioral profile content, may include dynamic content creation and/or may include physical control of devices which may affect the safety of a particular operator and/or user and/or individuals. In an embodiment, sensor content may comprise content from any of a wide range of possible sources and/or that may be variable. In an embodiment, a processor, such as a behavioral processing unit, may incorporate machine-learning (e.g., neural networks, etc.) at least in part to adapt to the presence and/or absence of one or more particular sensors while providing probabilities, for example, represented at least in part by behavioral profile content.

In an embodiment, machine-based decision-making, such as may be performed by decision-making device, system, and/or process 250, for example, may depend at least in part on an operator's current state and/or the operator's ability to relatively quickly respond to changes in the operator's state. A wide range of possible sensor types may provide content representative of various aspects of a particular operator's biological and/or behavioral state, and/or representative of one or more environmental factors and/or other external factors. In an embodiment, a processor, such as behavioral processing unit 200, may include a sensor parameter processing unit, such as sensor parameter processing unit 210. In an embodiment, a sensor parameter processing unit, such as sensor parameter processing unit 210, may obtain signals and/or states from one or more sensors, such as sensors 230, and/or may process signals and/or states from one or more sensors to combine, coordinate, normalize and/or otherwise condition signals and/or states from one or more sensors.

For example, a sensor parameter processing unit, such as sensor parameter processing unit 210, may prepare sensor content for further processing, such as via machine learning operations. In an embodiment, machine learning acceleration circuitry, such as machine learning acceleration circuitry 220, may, at least in part, process sensor content to infer a substantially current biological and/or behavioral state of a particular operator. For example, a camera sensor and/or the like may provide one or more signals and/or states to a sensor parameter processing unit, such as sensor parameter processing unit 210. Sensor parameter processing unit 210 may generate one or more parameters representative of pupil dilation, focal point, blink duration, and/or blink rate, or any combination thereof, for example.

In an embodiment, machine learning acceleration circuitry, such as machine learning acceleration circuitry 220, may generate, at least in part, a representation of a particular operator's biological and/or behavioral state, such as behavioral profile content 240. In an embodiment, behavioral profile content, such as behavioral profile content 240, may comprise a specified set of parameters that may be utilized by any of a wide range of machine-based (e.g., computing device-based) decision making systems, devices, and/or processes, such as decision-making device, system, and/or process 250. In an embodiment, behavioral profile content may include a plurality of parameters representative of focal point, excitement, anger, fear, fatigue, dehydration, or focus/distraction, or any combination thereof, in relation to a particular user. Behavioral profile content may further include, by way of additional non-limiting examples, parameters representative of pre-breakthrough, silent like, regret/error acknowledgment, hunger, sloppiness/precision, empathy, agitation, confusion, and/or social engagement level, or any combination thereof.

In an embodiment, behavioral profile content may comprise a specified set of parameters, such as at least a subset of those mentioned above, for example. In an embodiment, a processor, such as behavioral processing unit 200, may generate a set of parameters representative of behavioral profile content specified in a manner so as to provide content regarding a particular user's behavioral and/or biological state to any of a wide range of devices, systems, and/or processes for any of a wide range of purposes and/or applications. Further, such a set of specified behavioral profile content parameters may be utilized concurrently by any number of devices, systems, and/or processes.

In an embodiment, a processor, such as behavioral processing unit 200, may repetitively obtain sensor content and/or may repetitively generate behavioral profile content for a particular user. For example, sensor content may be gathered and/or otherwise obtained at regular and/or specified intervals, and/or behavioral profile content may be generated at regular and/or specified intervals. In an embodiment, one or more devices, systems, and/or processes may track behavioral profile content over a period of time, for example, such as to detect changes in behavioral profile content, for example.

In an embodiment, a processor, such as behavioral processing unit 200, may be advantageously utilized at least in part by dedicating computing resources to process sensor content, for example, and/or to generate behavioral profile content, such as 240, for a particular user. Further, by generating a specified set of parameters comprising behavioral profile content, such as 240, systems, devices, and/or processes may be relieved of responsibility for generating behavioral profile content and may, for example, concentrate on particular areas of expertise and/or specialization, for example. Further, development costs may be reduced for systems, devices, and/or processes at least in part due to having a specified set of behavioral profile content parameters available from a processor, such as behavioral processing unit 200.

In an embodiment, a processor, such as behavioral processing unit 200, may merge substantially real-time sensor content (e.g., behavioral and/or biological sensor content, or a combination thereof) with representations of prior relationships (e.g., known and/or determined connections between that which may be measured and/or human states). Also, in an embodiment, a processor, such as behavioral processing unit 200, may utilize machine learning techniques (e.g., neural networks, etc.) to map incoming sensor content representative of one or more aspects of an operator's biological and/or behavioral state. In an embodiment, a processor, such as behavioral processing unit 200, may include support for relatively more efficient coordination and/or processing of content obtained from a wide range of possible sources (e.g., combination of content from biological and/or behavioral sensors and/or content representative of other factors) to generate a specified set of parameters, such as behavioral profile content 240. Further, in an embodiment, one or more memory devices may be provided to store operator-dependent and/or operator-independent content to enable relatively quicker identification of state changes in a particular user.

In an embodiment, machine learning operations such as may be performed by a processor, such as behavioral processing unit 200, for example, may store user-specific content in one or more memory devices and/or may also store user-generic content (e.g., determined and/or substantially known relationships between sensor content and/or user states). In an embodiment, user-specific content and/or user-generic content may be processed, such as via machine learning operations, to generate one or more output state vectors, such as behavioral profile content 240.

In an embodiment, through a combination of content from one or more sensors, knowledge of determined and/or substantially known correlations and/or relationships, and/or machine learning, a processor, such as behavioral processing unit 200, may generate parameters representative of a substantially current behavioral and/or biological state of a particular user. In an embodiment, behavioral profile content, such as 240, may include one or more parameters indicative of scores, such as for user states such as anger, excitement, fatigue, distraction, etc. Further, utilization of relatively larger amounts of content from sensors may allow for improvements in a user state and/or may allow for better differentiation between user states. For example, in an embodiment, fear and/or excitement may both increase heart rate, but fear, without excitement, may result in restriction in a user's shoulders. A behavioral processing unit, such as 200, may differentiate between a user's fear and/or excitement based at least in part on content obtained from one or more cameras, in an embodiment. Of course, subject matter is not limited in scope in these respects.

In an embodiment, external factors may come in to play with respect to generating behavioral profile content and/or decision-making. For example, one or more parameters indicative of one or more external factors, such as external factor parameters 260, may be obtained by a behavioral profile unit, such as BPU 200, and/or by a decision-making device, system, and/or process, such as decision-making system 250. Parameters representative of external factors may include, for example, parameters representative of location, time of day, presence and/or identity of external individual, and/or general sentiment.

Figure 3:
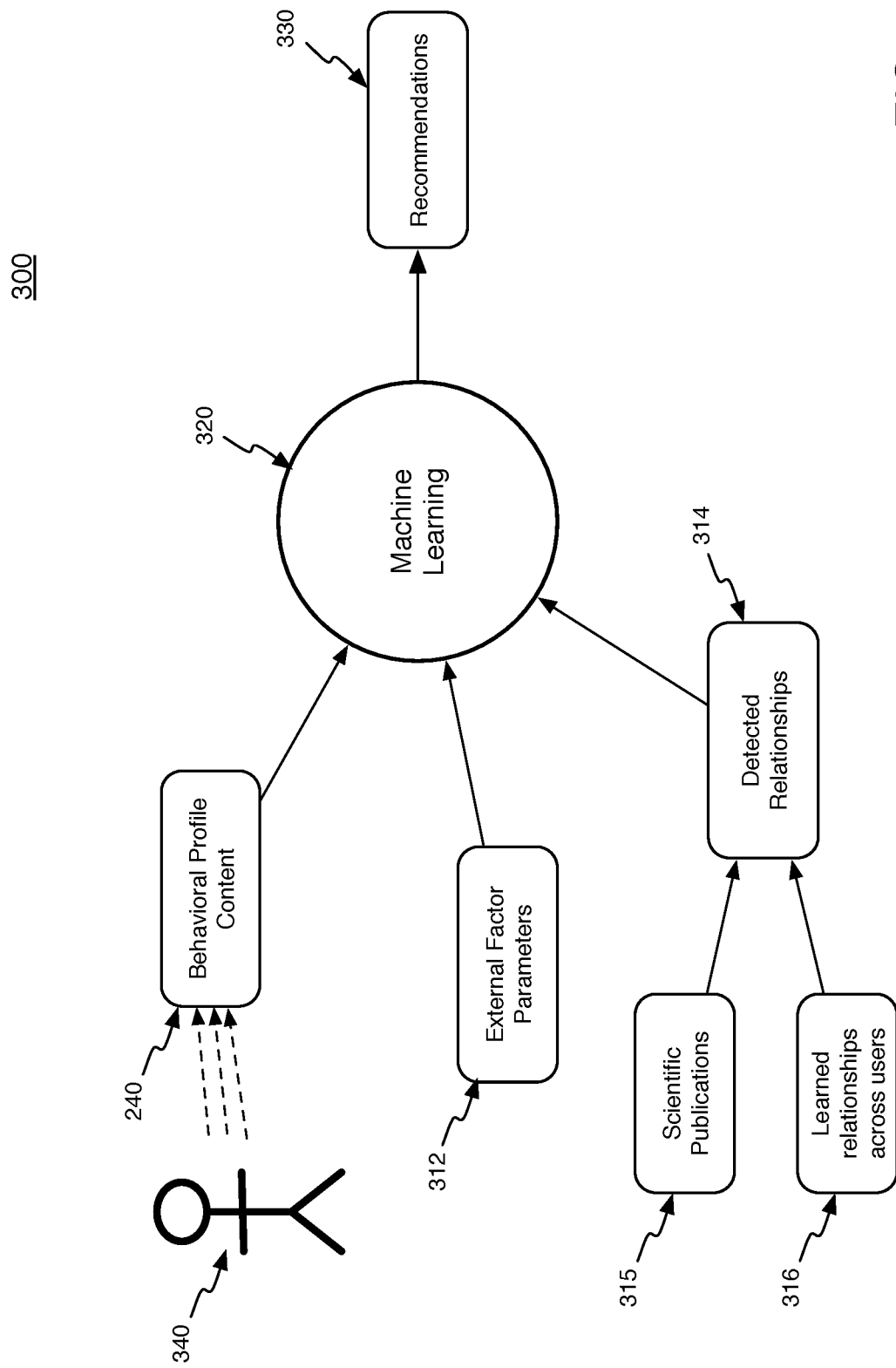
FIG. 3 is an illustration of an example device, system, and/or process for processing signals and/or states representative of behavioral profile content, in accordance with an embodiment.

FIG. 3 is an illustration of an embodiment 300 of an example device, system, and/or process for processing behavioral profile content, such as behavioral profile content 240, for any of a wide range of possible applications and/or purposes. As mentioned, a processor, such as behavioral processing unit 200, may generate behavioral profile content, such as behavioral profile content 240, based, at least in part, on sensor content, such as content from one or more of sensors 230. In an embodiment, behavioral profile content, such as behavioral profile content 240, may be utilized, at least in part, to evolve and/or tailor virtual reality and/or gaming and/or other content being consumed and/or to be consumed by a particular user/gamer, such as user 340, based, at least in part, on a current biological and/or behavioral state of a user/gamer, such as user 340. In this manner, for example, content, such as video game content, may be customized for a particular user/gamer, such as user 340, to relatively more effectively induce a desired state in the particular user.

For example, in an embodiment, content from one or more cameras pointed at a user's eyes, a microphone, a skin sensor to measure perspiration and/or temperature, one or more pressure sensors for the user's fingers, a heart rate monitor, a hydration sensor, and/or a breath monitor, or any combination thereof, may be utilized as part of an immersive gaming system. In an embodiment, a processor, such as behavioral processing unit 200, may obtain content from one or more sensors, such as one or more sensors mentioned above, and/or may generate a set of parameters, such as behavioral profile content 240, representative of a substantially current biological and/or behavioral state for a particular user/gamer. Sensor content obtained via a camera, for example, may be processed to generate behavioral profile content, such as behavioral profile content 240, representative of pupil dilation, focal point, blink duration, and/or blink rate, to name a few non-limiting examples. Further, digital audio content, such as may be obtained via a microphone, for example, may be processed to generate behavioral profile content, such as behavioral profile content 240, representative of volume, tone, and/or sentiment, for example.

In an embodiment, determined and/or substantially known relationships, such as relationship parameters 314, may include relationships between behavioral profile content and/or user states and/or may include scientifically determined relationships. In an embodiment, relationships between content that may be gleaned from sensor output and a user's behavioral and/or biological state may be determined, at least in part, via one or more scientific publications, such as scientific publications parameters 315. For example, pupil dilation may be linked with dopamine release according to one or more scientific publications, such from the National Institute of Health (NIH). Further, for example, dopamine release may be linked with anticipation and/or relatively heightened emotional response to stimulus according to one or more scientific studies, such as may be published by Nature research journal. In an embodiment, content representative of relationships gleaned from scientific publications may be stored in at least one memory, such as memory 130, for example, and/or may be provided to a device, system, and/or process for performing machine learning operations, such as depicted at machine learning 320.

In an embodiment, in addition to and/or instead of scientifically determined relationships, other relationships may be determined offline through content collection and/or machine learning. For example, test subjects, such as one or more users and/or operators, may provide behavioral and/or biological state content and/or may provide biological and/or behavioral marker content so that relationships between such biomarkers and behavioral and/or biological state content may be determined, such as learned relationships parameters 316. In an embodiment, biomarkers may be recorded for test subjects as they are presented with content and/or substances that aim to evoke a particular state, for example. Via machine learning, such as machine learning 320, a variety of biological and/or behavioral states for a user may be learned to be identified through biological and/or behavioral markers, in an embodiment.

In an embodiment, a device, system, and/or process, such as machine learning 320, may generate recommendations, such as recommendation parameters 330, based at least in part on behavioral profile content, such as behavioral profile content 240, for a particular user, such as user 340. In this context, "recommendations" refers to one or more indications of suggestions and/or actions that may be taken by one or more individuals, devices, systems, and/or processes. For example, recommendations, such as recommendation parameters 330, may include suggestions, presented to a particular user, directed to improving one or more aspects of particular user's behavioral and/or biological state. Also, for another example, recommendations, such as recommendation parameters 330, may indicate to a device, system, and/or process to alter content, such as video game and/or virtual reality content, being consumed and/or to be consumed by a particular user. Further, for example, recommendations, such as recommendation parameters 330, may configure and/or reconfigure a device, system, and/or process to alter a partitioning of responsibilities between an operator and a device, system, and/or process in a situation of shared responsibility (e.g., tech-assisted driving, flying, drone operations, etc.). Of course, claimed subject matter is not limited in scope in these respects.

As mentioned, in an embodiment, a gaming and/or virtual reality system may utilize behavioral profile content, such as behavioral profile content 240, for a particular user, such as user 340, to evolve content such that game and/or virtual content may be tailored to produce a desired effect in the particular user. For example, a device, system, and/or process, such as machine learning 320, may detect, based at least in part on behavioral profile content, such as behavioral profile content 240, a drop in a user's level of excitement. In an embodiment, a gaming system may respond to a drop in excitement level at least in part by altering content presented to the operator in an attempt to grab the operator's interest and/or to otherwise create an increase in operator interest level. Of course, responding to a user's change in level of interest is merely one way a gaming and/or virtual reality system may advantageously utilize behavioral profile content, such as behavioral profile content 240. Another example may include tailoring streaming content, such as Internet-based audio streaming, to induce a particular state in a particular user. For example, a streaming radio station (e.g., Pandora, Spotify, Apple Music, and/or the like) may alter content of a "relaxation" radio station and/or playlist based at least in part on behavioral profile content to induce a state of relaxation in the particular user. This may have particular advantages over generic relaxation-type content streams that are not tailored to particular individuals, over streams based on explicit user "likes," and/or over streams that don't take into account biological and/or behavioral states of a particular user.

For example, a content providing device, system, and/or process, such as a gaming and/or virtual reality system, for example, may present a particular user and/or particular group of users with content aimed to produce a specified state such as fear, excitement, relaxation, etc. Behavioral profile content, such as behavioral profile content 240, and/or such as may be generated by a behavioral processing unit, such as behavioral processing unit 200, for example, may be monitored to track various state levels for the user and/or group of users. In an embodiment, a content-providing device, system, and/or process may test various versions of content on the user and/or group of users to gain knowledge, via a behavioral processing unit, such as behavioral processing unit 200, for example, about a particular user and/or group of users. For example, a content provider may desire to test versions of content with respect to different levels of fear of snakes, zombies, etc. Of course, subject matter is not limited with respect to the types of fears and/or other behavioral and/or biological responses that may be tested.

In an embodiment, a content-providing device, system, and/or process may log content-state scores for individual users and/or groups of users. Content-state scores may be utilized, for example, by a content provider to select and/or generate user-specific content aimed at producing a desired state in particular users (e.g., replace spiders with snakes if a particular user indicates through behavioral profile content a greater fear of snakes). In an embodiment, such customizations may occur without the knowledge of a particular user, and/or a content-providing device, system, and/or process may continue to test and/or evolve over time based at least in part on detected changes in a particular user's evolving biological and/or behavioral state.

In an embodiment, customization of content based, at least in part, on a particular user's biological and/or behavioral state, such as indicated at least in part via behavioral profile content, such as behavioral profile content 240, that may be generated, for example, by a behavioral processing unit, such as behavioral processing unit 200, may be advantageously employed in targeted advertising systems, for example. In an embodiment, an advertisement, such as an online advertisement, may be generated and/or selected based, at least in part, on a particular user's biological and/or behavioral state, such as indicated at least in part via behavioral profile content, such as behavioral profile content 240. For example, a billboard presented to a particular user from within a video game may depict a soft-drink at least in part in response to a determination, based at least in part on the particular user's behavioral profile content, that the particular user may be dehydrated. Similarly, for example, an advertisement for a fast-food restaurant may be displayed to a user at least in part in response to a determination, based at least in part on behavioral profile content, that the user in hungry. Of course, these are merely example advertisements, and subject matter is not limited in scope in these respects.

Customization of advertisements based at least in part on behavioral profile content, for example, may further include determining advantageous points in time to display particular advertisements to particular users. For example, a particular advertisement for a particular brand may be timed, such as within a video game and/or other digital content, to coincide with a dopamine release and/or silent like, by way of non-limiting example, such that the particular user may associate his or her feelings of well-being with the advertised brand.

In another embodiment involving customization of content, such as adaptation of video game content based at least in part on behavioral profile content for one or more users, may include generating and/or selecting content based at least in part on multiple user's behavioral profile content. For example, in a video game system, if a particular user "1" is afraid of a particular game element "x" (e.g., as may be determined at least in part based on user 1's behavioral profile content) and if user "2" is afraid of a particular game element "y" (e.g., as may be determined at least in part based on user 2's behavioral profile content), and if a particular video game involves user 1 and user 2 collaborating to fight a monster, for example, a video game system may generate a monster comprised at least in part of elements x and y. Again, subject matter is not limited in scope to these particular examples.

In a further embodiment, customization of content based, at least in part, on a particular user's biological and/or behavioral state, such as indicated at least in part via behavioral profile content, such as behavioral profile content 240, may be advantageously employed in educational settings, for example. In an embodiment, educational content for a technology-assisted teaching system and/or for a virtual-reality based educational tool may be selected, altered, and/or otherwise tailored for one or more particular users based, at least in part, on the one or more particular user's biological and/or behavioral states. For example, educational content may be selected, altered, and/or otherwise tailored based at least in part on indications of pre-breakthrough, focus/distraction, and/or regret/acknowledgement. Similarly, for example, indications of empathy from behavioral profile content may provide for tailoring a virtual teacher such that a student may respond well to the virtual teacher.

In other embodiments, recommendations may be provided to a user, such as a gamer, to improve user wellness based at least in part on behavioral profile content, such as behavioral profile content 240. For example, embodiments may include identification of a biological condition, such as via monitoring and/or tracking behavioral profile content, for example, and may further include generation of suggestive content to encourage particular actions by a user outside of a gaming environment with a goal of improving user/gamer wellness. For example, if a system, device, and/or process, such as system, device, and/or process 320, determines from behavioral profile content, such as behavioral profile content 240, that a user, such as behavioral profile content 240, may be dehydrated, a message may be displayed and/or otherwise communicated to the user within a gaming and/or virtual reality environment as a reminder to take a break and/or to seek nourishment. Similar recommendations may be made with respect to food, sleep, medication, supplementation, etc. Further, game play may be altered and/or otherwise tailored based at least in part on a biological condition indicated at least in part via behavioral profile content, such as behavioral profile content 240. For example, if behavioral profile content, such as behavioral profile content 240, indicates that a user may be hungry, a content-providing system, such as a game system, may alter an avatar meeting spot from a park to a food establishment. Such an alteration may serve as a reminder to the user/gamer to seek nourishment.

In an embodiment, avatars and/or other game and/or virtual reality elements may be utilized to communicate recommendations to a particular gamer. For example, within a game and/or virtual reality environment, an avatar meeting may be arranged to take place within a restaurant and/or other food establishment to suggest that it may be time to adjust blood sugar. Further, in an embodiment, a user, such as a gamer, may provide indications to a gaming and/or virtual reality system, for example, such as via a user interface of a gaming system and/or other computing device. A content-providing system, such as a game system, may modify and/or otherwise tailor content at least in part in accordance with the user's inputs. For example, as user may provide inputs regarding the user's favorite snack foods, and those favorite snack foods may be incorporated into recommendations generated by the system regarding nourishment.

Also, in an embodiment, a device, system, and/or process, such as machine learning 320, may track performance changes with respect to a particular user, such as user 340. For example, in a collaborative task where a human operator and/or computer system may partition responsibilities (e.g., tech-assisted driving or flying), it may be desirable for the computer system to understand performance changes in the operator which may be indicative of the operator's ability to continue to have responsibility for a specific task. Similarly, in an adaptive gaming experience, a gaming system may make advantageous use of an indication that an operator may be performing above and/or below particular baselines. For example, a gaming system may tailor game content at least in part to take into account operator performance level.

In an embodiment, a performance test may be administered to a particular user/operator that may require actions in response to presented content. For example, a performance test might involve placing objects at various screen locations that may require interactions with relatively higher accuracy and/or introducing a challenging sequence that may require relatively rapid response. In an embodiment, such tests may be "hidden" in that a gamer, for example, may be unaware that they are being tested.

In an embodiment, an external system, such as a gaming and/or virtual reality system, may uniquely label and/or otherwise number performance tests. An external system may signal to a behavioral processing unit, such as BPU 200, a start of a performance test and/or may further provide a unique label and/or number associated with the particular performance test. BPU 200, for example, may track biological response (e.g. heart rate, perspiration, etc.) of a user for the performance test. Further, in an embodiment, the external system may indicate to BPU 200 the completion of the performance test, and BPU 200 may, in turn, provide relevant behavioral profile content back to the external. For example, a vector comprising score parameters may be provided and/or may be stored at the external system. By storing performance content over time for individual users/gamers, and perhaps incorporating machine learning, the external system may identify how a particular user/gamer may be performing compared to the individual's typical performance.

Embodiments may also be utilized to identify manipulation patterns within content being consumed by a user. In 1927, Ian Pavlov described humans' "biological orienting response" as an instinctive biological response to sudden movement and novel stimuli. This response may include a temporary block of alpha waves, increased blood vessel dilation to the brain, decreased heart rate, etc. Researchers later studied how various aspects of television content, including cuts, pans, edits, and zooms, for example, may activate a biological orienting response. Content creators may utilize techniques to intentionally hold a consumer's attention through rapid feature changes that may relatively frequently and/or continuously activate a consumer's orienting response. Such relatively frequent and/or continuous activation of an orienting response may result in addiction and/or other negative health consequences. Through monitoring of a user's biological and/or behavioral indicators, such as, for example, via tracking focal point shifts and/or heart rate drops, for example, embodiments may identify patterns that may be intended to activate an orienting response. Embodiments may further signal to a user that such manipulation may be occurring.

Further, with the possible input of additional biometric indicators obtained from users, more complex techniques and/or patterns may be developed (e.g., by the scientific community and/or the entertainment community) in an effort to keep a user engaged and potentially addicted. For example, a pattern, such as a focal point change every 4 seconds for 2 minutes, followed by dopamine release every 30 seconds for 2 minutes, etc., may be found to significantly increase a likelihood of user engagement for some particular amount of time. As such patterns and/or techniques become increasingly complex, a user may not be able to easily identify when he/she may be manipulated. In an embodiment, determined and/or known patterns of manipulation may be identified, at least in part, via tracking and/or monitoring of biological markers, such as via generation of behavioral profile content from sensor output. Embodiments may further signal the presence of such patterns to a user in real-time (e.g., substantially as they are occurring).

In embodiments, a user may be alerted, such as via a display 140, if a presentation of content (e.g., game, television show, movie, etc.) occurs within a context of determined and/or known manipulative techniques and/or patterns. By having a processor, such as BPU 200, for example, detect such manipulative techniques and/or patterns via, at least in part, processing of sensor content and/or generation of behavioral profile content, such as behavioral profile content 240, a user may focus attention on content being consumed without also attempting to detect manipulative techniques and/or patterns. For example, a user/consumer may be fully engaged in the content and may request to be notified in response to a detection of manipulative techniques and/or patterns. Users, such as gamers, for example, may generally benefit from such embodiments even if no request is made to be notified of detected manipulative techniques and/or patterns due at least in part to content providers potentially being encouraged (e.g., via possibility of exposure) to moderate utilization of such manipulative techniques and/or patterns. For example, just as the inclusion of calorie counts on menus may create an incentive for restaurants to moderate calorie amounts, identification of manipulation techniques and/or patterns may encourage content developers to moderate the use of manipulative techniques and/or patterns. Further, embodiments may incorporate manipulative pattern detection as part of a parental control system, for example.

Additional embodiments may include machine learning devices, systems, and/or processes for managing potential addiction and/or potential resulting negative consequences through gamer-identified boundary-crossing states. In an embodiment, a gamer/user may explicitly indicate, such as via an input to a computing device, such as mobile device 100, that the gamer has entered a "boundary crossing state". For example, in a situation wherein the user may have stayed up too late playing, or wherein the user may have forgotten an appointment, or wherein the user may recognize having passed a point of needing to eat, etc., the user may explicitly indicate such a situation via interaction with a user interface of a computing device, such as mobile device 100. Based at least in part on the user's inputs regarding boundary-crossing states, a processor, such as BPU 200, may utilize machine-learning and/or other analysis techniques to recognize and/or identify behavioral patterns associated with entering a boundary crossing state. In an embodiment, a computing device, such as mobile device 100, may notify a user at least in part in response to an identification of a pattern likely to induce a boundary crossing state so that the user may take appropriate steps (e.g., stop playing a particular game) to avoid the boundary-crossing state and/or undesirable consequences.

Further, embodiments may include user notification of recommended health cues as they are being communicated to a content-providing system, such as a game system. For example, a user may request to be alerted in response to a processor, such as BPU 200 and/or processor 110, generating recommendations, such as recommendations 330, to be communicated to a content provider. For example, in situations where recommendation parameters, such as parameters 330, may be provided to a content provider to have the content provider embed suggestive content related to, for example, dehydration, notification may also be provided to a user, such as via display 140, for example, independent of a game and/or content provider. Such direct-to-user communication may help address a situation wherein a user may otherwise be dependent on suggestive content from a content-providing system, such as a game system, to signify actions that may improve user wellness. Additionally, such embodiments may provide a user some visibility into in-game targeted advertising that may be influenced by the user's behavioral and/or biological state.

Further, in an embodiment, performance degradation may be predicted by biological changes. In computer assisted driving, for example, a human operator may be staying within their particular lane at 3:00 PM and at 3:00 AM, but stress levels may increase significantly by 3:00 AM. A behavioral processing unit, such as BPU 200, may detect such biological indicators of stress at least in part through content obtained from one or more sensors. In an embodiment, detection of biological stress indicators and/or performance test content may be utilized in combination to predict an imminent hazardous condition and/or to make recommendations and/or to take other appropriate action.

In another embodiment, behavioral profile content, such as behavioral profile content 240, provided, for example, by a behavioral processing unit, such as behavioral processing unit 200, may be utilized to help manage a user's mental health. For example, as mentioned, external factors may come in to play with respect to generating behavioral profile content and/or decision-making, in an embodiment. For example, one or more parameters indicative of one or more external factors, such as external factor parameters 312, may be obtained by a behavioral profile unit, such as BPU 200, and/or by a decision-making device, system, and/or process, such as machine learning 320. Parameters representative of external factors may include, for example, parameters representative of location, time of day, presence, identity, and/or state of external individual, and/or general sentiment. By using external information, such as an individual's location, the time of day, the presence, identity, and/or state of other individuals, and/or sentiment analysis from always-on environmental microphones and/or other sensors, for example, machine-learning-based computer intelligence, such as performed at least in part by BPU 200 and/or decision-making device, system, and/or process 250, may identify patterns and/or recommend actions for a particular individual (e.g. suggest changing location), recommend actions for another person (e.g. suggest to a friend to call and check-in), and/or preempt actions with potential consequences (e.g. suggest reconsidering calling a family member at this moment.) A goal of one or more embodiments may be to recommend action and/or inaction to improve levels of emotional states (e.g., reduce undesirable states and increase desirable ones).

In an embodiment, presence, identity, and/or state of one or more external individuals may be determined, at least in part, via obtaining one or more signals and/or states from one or more external individual's personal computing devices. In other embodiments, a behavioral processing unit, such as BPU 200, may be utilized to determine a presence, identity, and/or state of one or more external individuals. For example a behavioral processing unit, such as BPU 200, may determine presence, identity, and/or state of one or more external individuals at least in part via voice monitoring (e.g., analysis of signals and/or states generated by a microphone), via detection of phone calls between a user and one or more particular external individuals, through detection of user interaction with one or more individual user's social media content, and/or via detection and/or monitoring of user discussion of one or more external individuals via phone calls, social media posts, email text, and/or audible conversation related to one or more external individuals, for example. In an embodiment, presence, identity, and/or state of an external individual may be determined, at least in part, via monitoring of personal user interactions with an external individual and/or via monitoring of a user's characterization, explicit and/or implied, of an external individual. In an embodiment, monitoring of personal user interactions with an external individual and/or monitoring of a user's characterizations of an external individual may be performed, at least in part, by a behavioral processing unit, such as BPU 200, based at least in part on sensor content, such as content from sensors 230, for example.

Subtle patterns sometimes exist between changes in an individual's mental/emotional state and external factors, such as consumption of certain foods, various social interactions, and/or interaction with various media outlets (e.g., television, radio, and/or websites). Non-desirable emotional states may continue to produce societal impacts that may manifest as violence at home and/or in schools, as well as addiction and/or suicide rates. Embodiments may enable identification of subtle patterns that may lead to undesirable emotional states such as anger, and recommendations may then be made to preempt an individual from progressing to an undesirable mental state and/or to return to a more desirable mental state.

In one example, domestic violence and/or other abuse may be averted at least in part by identifying a pattern, such as more than three hours at a particular location (e.g. a bar, indicating alcohol consumption) followed by eating at a particular restaurant (e.g., steakhouse, indicating red meat consumption) which may correlate with increased anger later in the evening. Embodiments may recommend that one leave the particular location and/or advise an individual to be on alert for increasing anger, for example.

As mentioned, a state of an external individual may be provided by a behavioral processing unit, such as BPU 200. For example, behavioral profile content generated by BPU 200 may include one or more parameters representative of an emotional, behavioral, and/or biological state of one or more particular external individuals. In some situations, for example, incorporation of content representative of an external individual's state may significantly improve the utility and/or quality of various embodiments. For example, without the state of an external individual, a machine-learning device, system, and/or process, such as machine-learning 320, may generate a recommendation, such as recommendation 330, indicating that it may be ill-advised for the user to call the user's sister on Tuesday evenings because calling her during that time has negatively affected the user's mental state. Generally, in this example, the user's sister has a big meeting on Tuesdays, and on Tuesday evenings she is stressed and quick to anger, leading to increased anger for the user. However, for this example, when the Tuesday meeting is cancelled, the user's sister may not be stressed and/or quick to anger. By utilizing content representative of the external individual's mental and/or emotional state, for example, as input, a machine-learning device, system, and/or process, such as machine-learning 320, may generate an improved recommendation, such as recommendation 330, with respect to re-thinking a phone call to the user's sister. For example, because machine-learning 320 is provided input indicating that the user's sister is not presently stressed and/or is not showing indications of anger, machine-learning may recommend, such as via recommendation parameters 330, that the user go ahead and place the phone call. Further, for example, warnings regarding placing phone calls to the user's sister may be reserved for situations in which the sister is actually showing stress and/or anger. Of course, this is merely an example of how a state of an external individual may be detected and/or utilized, and claimed subject matter is not limited in scope in these respects.

Additionally, embodiments may include sharing of behavioral profile content, such as behavioral profile content 240, and/or recommendations, such as recommendations 330, among groups of individuals. For example, individual members of a group of individuals may have personal computing devices, such as mobile devices 100, for example, that may incorporate sensors, such as sensors 150, camera 160, and/or microphone 170, and that may also incorporate a behavioral processing unit, such as BPU 200. In an embodiment, behavioral profile content, such as behavioral profile content 240, and/or recommendations, such as recommendations 330, for individual members of a group may be shared within the group. Behavioral profile content, such as behavioral profile content 240, and/or recommendations, such as recommendations 330, for a particular individual may be transmitted, such as via signal packets in a cellular network, wireless local area network, and/or any of a wide range of other wired and/or wireless communication technologies, for example, to personal computing devices of one or more other members of the group. For example, friends and/or family may be linked via their respective personal computing devices (e.g., mobile devices 100) for purposes of collaborative health management, for example, such that their respective state vectors (e.g., behavioral profile content 240 and/or recommendations 330) may be used as inputs to be utilized by behavioral processing units, such as BPU 200, and/or by a decision-making device, system, and/or process, such as decision making system 250, and/or by a machine-learning device, system, and/or process, such as machine-learning 320.

By sharing behavioral profile content and/or recommendations, at least in part, among individuals of a group of individuals, more complex patterns and/or interactions between the particular individuals of the group may be monitored and/or tracked, thereby improving the quality of suggestions and/or recommendations, such as recommendations 330. For example, if two parents and a child are linked, embodiments identify that it was not any pattern of the child that resulted in the child entering into an undesirable mental state, but rather it was a pattern associated with one or both of the parents. Embodiments wherein behavioral profile content and/or recommendations may be shared among various groups of individuals, such as within a family, may be utilized to avert and/or warn of violence and/or abuse, such as domestic violence and/or abuse, for example.

For example, a user and the user's significant other (e.g., spouse, domestic partner, boyfriend, girlfriend, etc.) may each have respective personal computing devices, such as mobile device 100. In an embodiment, the user's personal computing device and the significant other's personal computing device may share behavioral profile content and/or recommendations, at least in part, between the two devices. That is, the two personal computing devices may be "linked." In an embodiment, a user's personal computing device, such as mobile device 100, may recommend, such as via visual content presented to the user via display 140 and/or via an audio output, to change locations to avoid a situation of potential domestic abuse. In an embodiment, such a recommendation may be based, at least in part, on behavioral profile content, such as behavioral profile content 240, and/or recommendations, such as recommendations 330, obtained from a significant other's personal computing device.

Figure 4:
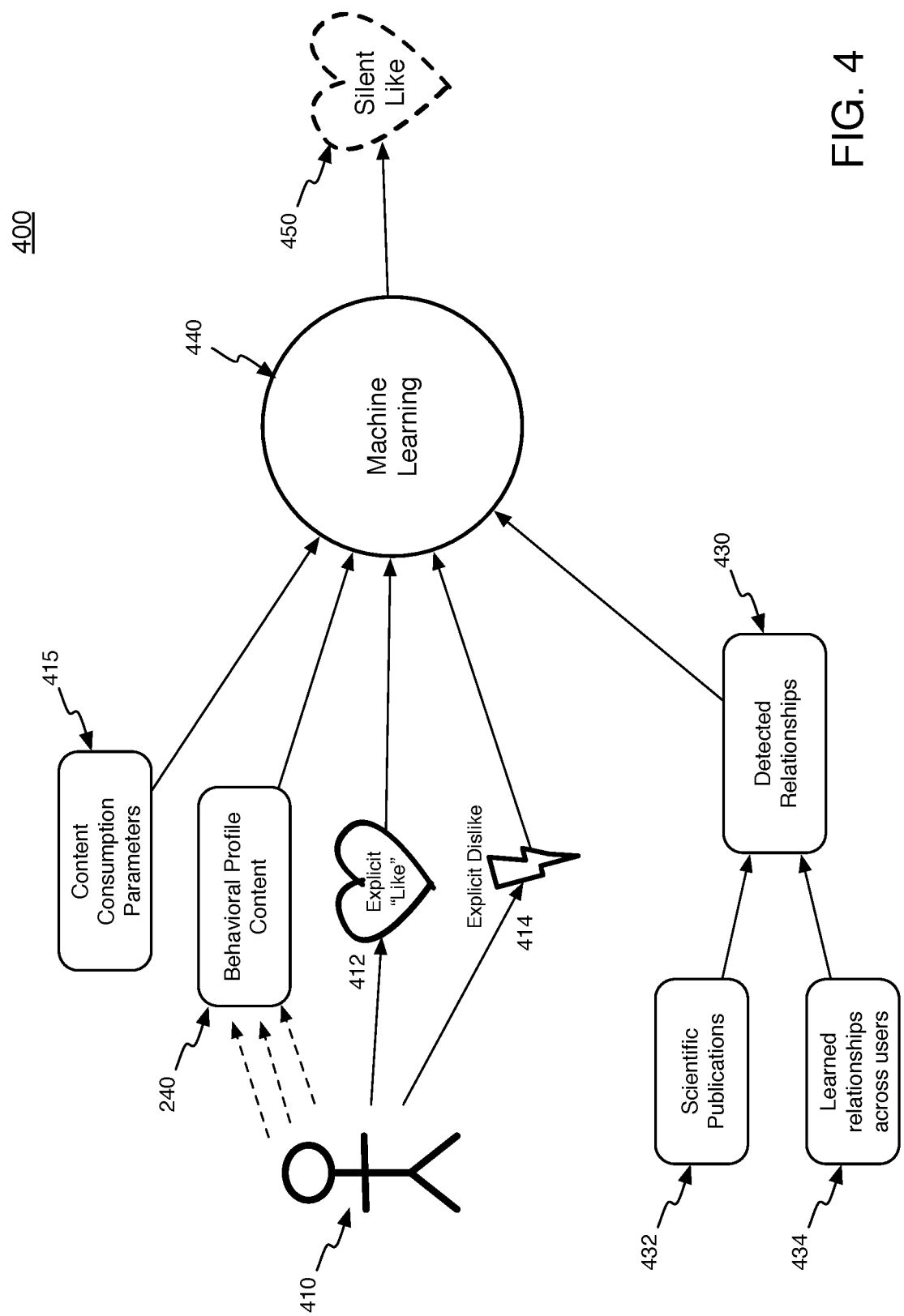
FIG. 4 is an illustration of an example device, system, and/or process for processing signals and/or states representative of behavioral profile content, in accordance with an embodiment.

FIG. 4 is an illustration of an embodiment 400 of an example device, system, and/or process for processing signals and/or states representative of behavioral profile content. In an embodiment, machine learning and/or artificial intelligence and/or other techniques, such as machine learning 440, may detect "silent likes," and/or may generate one or more parameters indicative of silent likes, such as silent like parameters 450. As mentioned, silent likes refer to at least partially non-explicit indication of approval, enjoyment, etc. of content consumed by a particular user, such as user 410. For example, one or more sensors may detect one or more behaviors and/or biological aspects of a particular user (e.g., head bobbing, pupil dilation indicating dopamine release, etc.) that may be understood to indicate approval, enjoyment, etc. of content being consumed by the particular user. Other biological and/or behavioral aspects of a particular user that may indicate liking currently-consumed digital content, for example, may include, by way of non-limiting examples, head movement, voice volume, heart rate, breath, perspiration, blood pressure, eye movement, blink rate, pupil dilation, etc. In an embodiment, substantially understood relationships, such as dopamine release and/or pupil dilation, and/or relatively recently and/or substantially currently determined and/or learned relationships may be utilized at least in part to determine silent likes.

In an embodiment, machine learning and/or artificial intelligence and/or other techniques, such as machine learning 440, may obtain behavioral profile content, such as behavioral profile content 420, which may include one or more parameters indicative of a particular user's substantially current behavioral and/or biological state. Further, machine learning and/or artificial intelligence and/or other techniques, such as machine learning 440, may obtain parameters representative of content substantially currently being consumed by a particular user, such as user 410. For example, a user, such as user 410, may watch a movie that may be obtained from a streaming service. Content, such as content consumption parameters 415, identifying the movie, for example, may be provided to machine learning and/or artificial intelligence and/or other techniques, such as machine learning 440. In an embodiment, machine learning and/or artificial intelligence and/or other techniques, such as machine learning 440, may process behavioral profile content, such as behavioral profile content 420, and/or content consumption parameters, such as content consumption parameters 415, to determine whether a user, such as user 410, is indicating via some behavioral and/or biological aspect that a particular user approves and/or enjoys the particular content (e.g., movie, music, video game, etc.) being consumed by the particular user. In an embodiment, signals and/or states indicative of the particular user's silent like may be communicated to a content provider, for example. In this manner, a user's level of approval and/or enjoyment of particular content may be taken into account in recommending future content for the particular user. Example benefits of detecting "silent likes" may include obtaining "likes" from a user without requiring explicit user input that may disrupt an immersive experience. Without an ability to detect silent likes, either explicit likes would need to be obtained from a user or such indications from a user would not be obtained at all. Of course, subject matter is not limited in scope to these particular examples.

Further, in an embodiment, parameters indicative of determined and/or substantially known relationships, such as detected relationship parameters 430, may include parameters indicative of relationships between behavioral profile content and/or user states and/or may include parameters indicative of scientifically determined relationships. In an embodiment, relationships between content that may be gleaned from sensor output and a user's behavioral and/or biological state may be determined, at least in part, based at least in part on parameters representative of one or more scientific publications, such as scientific publication parameters 432. In an embodiment, parameters representative of other relationships, such as parameters 434, may be determined across multiple users.

To train a machine learning device, system, and/or process, such as device, system, and/or process 440, parameters indicative of explicit "likes" and/or "dislikes," such as parameters 412 and/or 414, may be obtained from one or more users, such as particular user 410, and/or may further obtain content consumption parameters, such as consumption parameters 415. A machine learning device, system, and/or process, such as machine learning device, system, and/or process 440, may correlate parameters indicative of obtained explicit "likes" and/or "dislikes" with changes in behavioral profile content, such as behavioral profile content 420, to train one or more machine learning parameters. In an embodiment, one or more users may provide explicit likes and/or dislikes by way of appropriate selection, such as via clicking, of particular elements of a web page, for example.

In an example embodiment, digital content providers, such as digital audio content providers Pandora and/or Spotify, for example, may select and/or evolve content to present to a particular user, such as user 410, based at least in part on behavioral profile content, such as behavioral profile content 420, obtained from a processor, such as behavioral processing unit 200, rather than and/or in addition to basing such determinations on explicit and/or limited "like" or "dislike" inputs obtained from a user. For example, digital audio content providers may modify playlists and/or streaming audio content for a particular user based at least in part on parameters indicative of silent likes, such as 450, in an embodiment.

Although some embodiments described above discuss silent likes in connection with consumption of content by a particular user, for example, subject matter is not limited in scope in this respect. For example, physiological arousal may play a role in occupational therapy for children with autism and/or attention deficit, hyperactivity (ADHD) disorders. Embodiments of devices, systems, and/or processes, such as those described herein, for example, may detect changes in electrodermal activity in children, for example, at least in part by obtaining signals and/or states from wearable sensors that may measure motion and/or one or more biological aspects.

Figure 5:
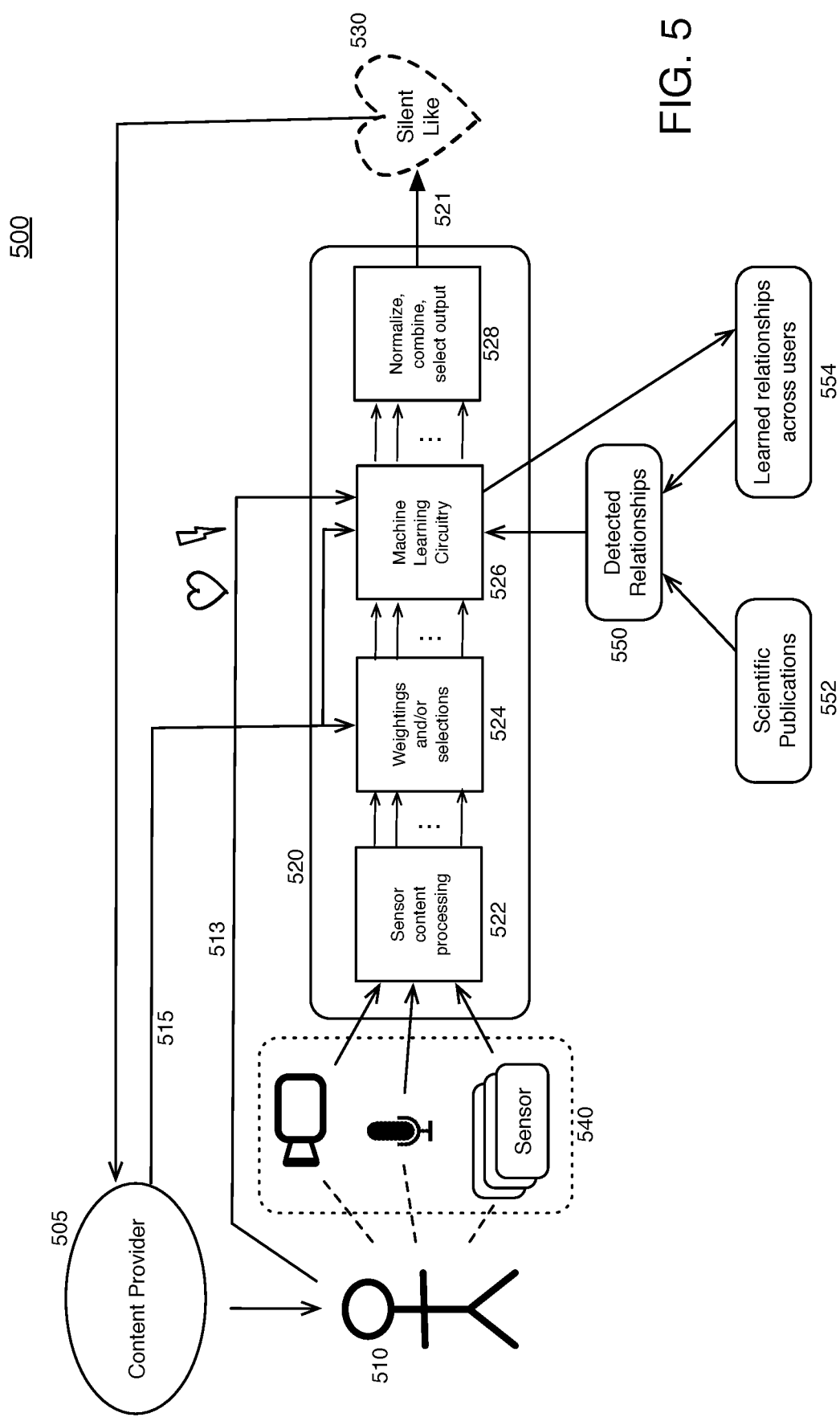
FIG. 5 is an illustration of an example device, system, and/or process for processing signals and/or states representative of behavioral profile content, in accordance with an embodiment.

FIG. 5 is an illustration of an embodiment 500 of a system, including a processor, such as a behavioral processing unit 520, to process signals and/or states representative of behavioral content in a computing device. In an embodiment, to generate behavioral profile content, such as behavioral profile content 521, for a particular user, such as user 510, a processor, such as behavioral processing unit 520, may obtain signals and/or states representative of content from one or more sensors, such as one or more of sensors 540. Also, in an embodiment, a processor, such as behavioral processing unit 520, may process sensor content, such as content from one or more of sensors 540, to generate behavioral profile content, such as behavioral profile content 521, for a particular user. In an embodiment, a processor, such as behavioral processing unit 520, may include behavioral content processing circuitry. For example, a processor, such as behavioral processing unit 520, may include sensor content processing circuitry, such as circuitry 522, and/or may include machine learning circuitry, such as circuitry 524 and/or 526, in an embodiment.

In an embodiment, a processor, such as behavioral processing unit 520, may provide circuitry to generate, at least in part, behavioral profile content, such as behavioral profile content 521, for a particular user, such as user 510, to be utilized for any of a wide range of possible applications and/or purposes. For example, a processor, such as behavioral processing unit 520, may generate behavioral profile content, such as behavioral profile content 521, to, at least in part, determine "silent likes" such as may be related to a particular user's consumption of digital media. In an embodiment, behavioral profile content, such as behavioral profile content 521, may include one or more parameters indicative of a silent like, such as one or more silent like parameters 530. Of course, this is merely one example of how behavioral profile content, such as behavioral profile content 521, generated by a processor, such as behavioral processing unit 520, may be utilized, and subject matter is not limited in these respects.

In an embodiment, one or more sensors, such as sensors 540, may provide content representative of various aspects of a particular operator's biological and/or behavioral state, and/or representative of one or more environmental factors and/or other external factors. In an embodiment, sensors 540 may include one or more sensors of one more sensor types, as previously mentioned. Further, in an embodiment, a processor, such as behavioral processing unit 520, may include circuitry, such as circuitry 522, to process content obtained from one or more sensors, such as sensors 540. In an embodiment, content obtained from sensors, such as sensors 540, may include digital signals and/or states, analog signals and/or states, or any combination thereof. For example, circuitry 522 may include digital circuitry, analog circuitry, or a combination thereof. In an embodiment, sensor content processing circuitry, such as circuitry 522, may convert one or more analog signals to digital signals, although subject matter is not limited in scope in this respect. In an embodiment, circuitry, such as circuitry 522, may process signals and/or states from one or more sensors, such as sensors 540, to combine, coordinate, normalize, amplify, filter, and/or otherwise condition signals and/or states from one or more sensors, such as sensors 540, although subject matter is not limited in scope in these respects.

Further, in an embodiment, a processor, such as behavioral processing unit 520, may include circuitry for determining and/or selecting weighting parameters and/or for determining and/or selecting particular machine learning devices, systems, and/or processes. For example, circuitry 524 may determine and/or select one or more particular machine learning techniques, such as one or more particular neural networks and/or including one or more weighting parameters, for example, for use in machine learning operations. In an embodiment, determination and/or selection of weighting parameters and/or machine learning operations, including one or more neural networks, for example, may be based, at least in part, on content, such as parameters 515, identifying one or more aspects (e.g., title, genre, content type, such as music, interactive game, video, etc.) of content consumed by a particular user, such as user 510. In an embodiment, parameters, such as parameters 515, indicative of one or more aspects of content consumed by one or more particular users, such as user 510, may be provided by one or more content providers, such as content provider 505. In an embodiment, content providers, such as content provider 505, may include, for example, a digital video content provider, digital audio content provider, video game content provider, virtual reality content provider, etc., although subject matter is not limited in scope in these respects.

In an embodiment, machine learning circuitry, such as machine learning circuitry 526, may, at least in part, process content, such as may be obtained from circuitry 522 and/or 524, to determine, estimate, and/or infer, for example, one or more parameters representative of a substantially current biological and/or behavioral state of a particular user. In an embodiment, machine learning circuitry, such as machine learning circuitry 526, may generate, at least in part and/or with contribution from output generation circuitry 528, a representation of a particular user's biological and/or behavioral state, such as behavioral profile content 521. In an embodiment, behavioral profile content, such as 521, may include a plurality of parameters representative of focal point, excitement, anger, fear, fatigue, dehydration, or focus/distraction, pre-breakthrough, silent like, regret/error acknowledgment, hunger, sloppiness/precision, empathy, or social engagement level, or any combination thereof, for example. In an embodiment, a processor, such as behavioral processing unit 520, may repetitively and/or substantially periodically obtain sensor content and/or may repetitively and/or substantially periodically generate behavioral profile content, such as behavioral profile content 521, for a particular user, such as user 510.

In an embodiment, a processor, such as behavioral processing unit 520, may determine appropriate weights for various sensor combinations and/or for particular parameters, such as parameters 515, provided by one or more content providers, such as content provider 505, during offline training operations, for example. In another embodiment, during online operation, for example, a set of inputs may be logged and/or later used as training parameters. For example, a user, such as user 510, may provide explicit likes and/or dislikes, such as may be represented as parameters 513, for particular content provided and/or suggested by one or more content providers, such as content provider 505. Further, in an embodiment, determined and/or substantially known relationships, such as represented by parameters 550, may include relationships between behavioral profile content and/or user states and/or may include scientifically determined relationships. For example, parameters, such as parameters 552, indicative of relationships between content that may be gleaned from sensor output and a user's behavioral and/or biological state may be determined, at least in part, via one or more scientific publications. In an embodiment, parameters, such as parameters 554, representative of other relationships may be determined across multiple users and/or across populations, for example.

Although embodiment 500 is described as detecting silent likes, for example, claimed subject matter is not limited in scope in this respect. For example, BPU 520 may be utilized to generate behavioral profile content and/or to perform decision-making and/or to make recommendations for any of a wide range of applications, such as example applications described herein.

Figure 6:
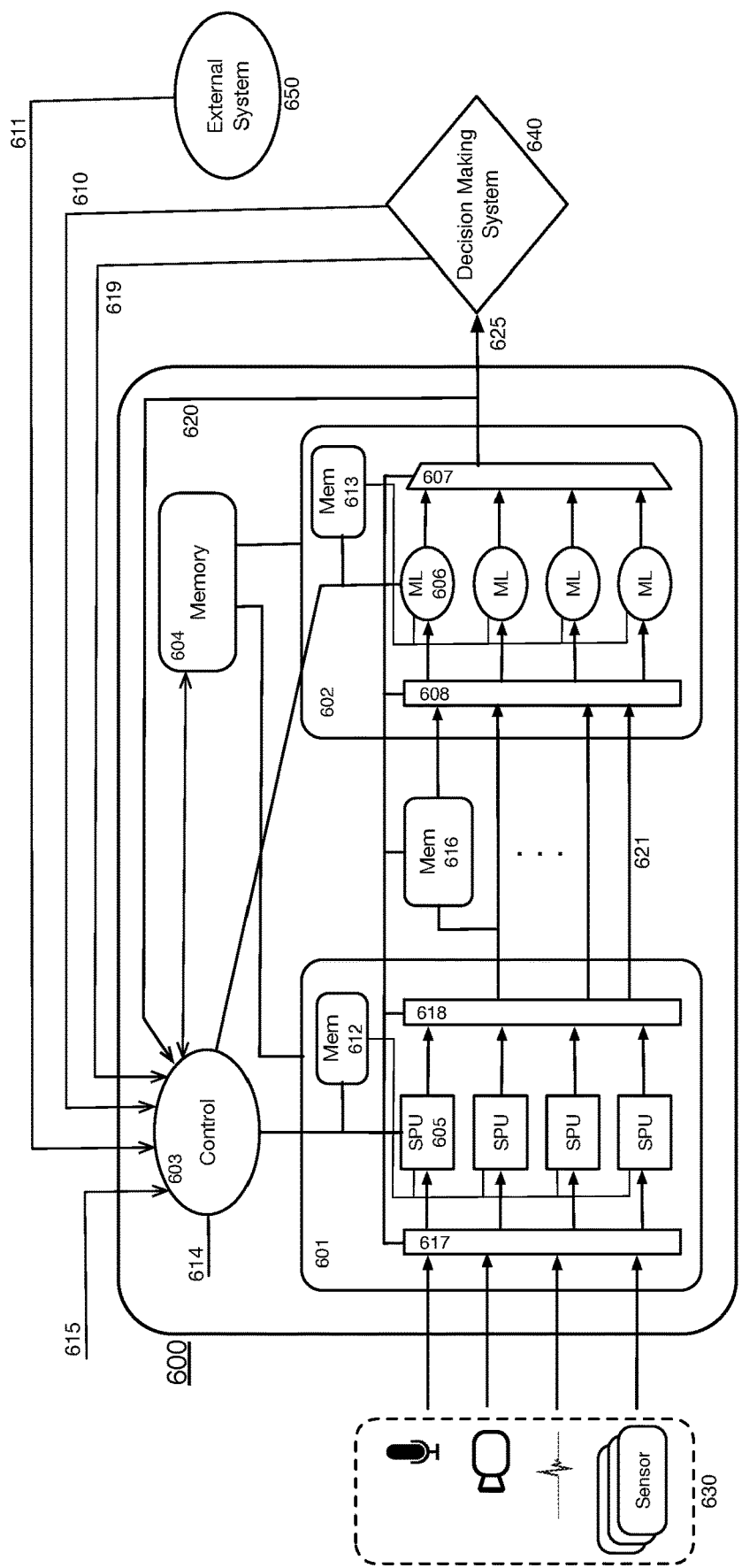
FIG. 6 is a schematic block diagram depicting an example processor for processing signals and/or states representative of behavioral profile content in a computing device, in accordance with an embodiment.

FIG. 6 is a schematic block diagram depicting an embodiment 600 of an example device, such as a behavioral processing unit, for processing content, such as content obtained from sensors 630, to generate signals and/or states representative of behavioral content in a computing device. In an embodiment, a processor, such as behavioral processing unit 600, may process digital signals and/or states or analog signals and/or states, or a combination thereof (e.g., mixed-signal). Any of a wide range of digital and/or analog circuit types may be utilized to process digital, analog, and/or mixed-signal signals and/or states, as explained more fully below. In an embodiment, one or more aspects of a processor, such as behavioral processing unit 600, may be implemented to operate in an analog domain, while one or more other aspects may be implemented to operate in a digital domain. In other embodiments, a processor, such as behavioral processing unit 600, may be implemented to operate substantially wholly in the digital domain and/or the analog domain.

In an embodiment, a processor, such as behavioral processing unit 600, may, in general, substantially continuously obtain content from sensors, such as one or more sensors 630, and/or may substantially continuously generate output signals and/or states, such as behavioral profile content 625. Generated output signals and/or states, such as behavioral profile content 625, may be made available to one or more decision-making systems, such as decision-making system 640, for example.

In an embodiment, a sensor parameter processing stage, such as sensor parameter processing stage 601, may obtain signals and/or states (e.g., digital, analog, and/or mixed-signal) from one or more sensors, such as sensors 630. In an embodiment, a sensor parameter processing stage, such as sensor parameter processing stage 601, may process signals and/or states from one or more sensors at least in part by combining content, adjusting timing, performing noise reductions and/or other signal reduction operations, normalizing content, or any combination thereof, for example. However, claimed subject matter is not limited in scope in this respect.

Further, in an embodiment, sensor content steering circuitry, such as sensor content steering circuitry 617, may direct signals and/or states obtained from sensors, such as from sensors 630, to one or more sensor processing units, such as one or more of sensor processing units (SPU) 605. In an embodiment, sensor processing units, such as SPUs 605, may be configured via one or more control signals, such as control signals communicated between a control unit, such as control unit 603, and sensor processing units, such as SPUs 605. Sensor processing units, such as SPUs 605, may prepare sensor content, such as signals and/or stated obtained from one or more sensors, such as sensors 630, for further processing by, for example, a machine-learning processing stage, such as machine-learning processing stage 602. In an embodiment, sensor content steering circuitry, such as sensor content steering circuitry 617, may direct content based, at least in part, on one or more control signals obtained from a control unit, such as control unit 603, and/or from a memory, such as memory 612, for example.

In an embodiment, a sensor processing stage, such as sensor processing stage 601, may include one or more sensor processing units, such as sensor processing units 605, that may be configured to operate individually or in one or more various combinations. Sensor processing units, such as SPUs 605, may perform, individually and/or in cooperation, any of a variety of operations that may be specified and/or implemented. Such operations may include, for example, combining signals and/or states, adjusting timing of signals and/or states, performing noise reductions and/or other signal reduction operations, and/or normalizing content, to list but a few examples.

One or more sensor processing units, such as SPUs 605, may be implemented to operate in an analog domain and/or one or more units may be implemented to operate in a digital domain. In an embodiment, sensors, such as sensors 630, may provide signals and/or states comprising analog signals and/or comprising digital content (e.g., signals and/or states). Further, in an embodiment, one or more analog signals obtained by one or more sensors, such as 630, may be converted to digital content using analog-to-digital conversion circuitry. In other embodiments, analog signals obtained from sensors, such as sensors 630, for example, may be maintained as analog signals for processing by one or more sensor processing units, such as SPUs 605. Further, in an embodiment, individual sensor processing units, such as SPUs 605, may be implemented in analog and/or digital based, at least in part, on particular tasks to be performed by a particular SPU and/or based, at least in part, on particular signal types to be obtained from sensors, such as sensors 630. In an embodiment, one or more of a variety of filters, signal amplifiers, and/or signal damping circuits, ranging from relatively more simple to relatively more complex, for example, may be performed by one or more particular sensor processing units, such as SPUs 605. Sensor processing unit operations, such as example operations mentioned herein, may have particular relevance in a larger context of behavioral profile content generation in connection with one or more machine-learning units. For example, sensor processing unit operations may be performed with an end-goal of behavioral profile content generation in mind.

In an embodiment, a particular sensor processing unit, such as SPU 605, may include noise reduction, filtering, dampening, combining, amplifying circuitry, etc., for example, implemented to operate in the analog domain. Analog circuitry may include, for example, one or more op-amps, transistors, capacitors, resistors, etc., although claimed subject matter is not limited in scope in this respect. Circuitry, such as noise reduction, filtering, dampening, combining, amplifying circuitry, etc., for example, may also be implemented in the digital domain, or in a combination of analog and/or digital. For another example, a particular sensor processing unit, such as a particular SPU 605, may be implemented in analog and/or digital to combine signals and/or states. In an embodiment, a unit to combine signals and/or states may be implemented in the analog domain or in the digital domain, or a combination thereof. In an embodiment, analog hysteretic "winner-take-all" circuits may be implemented at least in part to improve noise robustness and/or to mitigate, at least in part, timing difference between sensor input streams, for example. Of course, subject matter is not limited in scope in these respects. Further, noise reduction, filtering, dampening, combining, and/or amplifying are merely example tasks that may be performed by one or more sensor processing units, such as SPUs 605, and, again, claimed subject matter is not limited in scope in these respects.

Further, in an embodiment, sensor processing units, such as SPU 605, may be implemented to generate outputs that may exhibit a range of approximation, imprecision, and/or non-replicability. In an embodiment, machine-learning units, such as ML 606, may help mitigate consequences that might otherwise occur due to approximation, imprecision, and/or non-replicability potentially exhibited by sensor processing units, such as SPU 605. As utilized herein, "replicable" in the context of sensor processing units, such as SPU 605, refers to an ability to generate the same output for a given duplicate set of inputs. "Non-replicability" in this context refers to one or more sensor processing units, such as SPU 605, not necessarily generating the same output for a given duplicate set of inputs. That is, in an embodiment, one or more sensor processing units, such as SPU 605, may be implemented in a manner so as to not guarantee similar outputs for similar sets of inputs.

In an embodiment, content steering circuitry, such as content steering circuitry 618, may direct content, such as signals and/or states, generated by one or more sensor processing units, such as SPUs 605, to a machine-learning stage, such as machine-learning stage 602. Content, such as signals and/or states 621, generated by one or more sensor processing units, such as SPUs 605, may also be stored, at least temporarily, in a memory, such as memory 616, for example. In an embodiment, memory 616 may comprise a buffer, such as a first-in, first-out buffer, for example, although claimed subject matter is not limited in scope in this respect. In an embodiment, content steering circuitry, such as content steering circuitry 618, may direct content based, at least in part, on one or more control signals obtained from a control unit, such as control unit 603, and/or from a memory, such as memory 612, for example.

A machine-learning stage, such as machine-learning stage 602, may include content steering circuitry, such as content steering circuitry 608, that may direct content, such as signals and/or states 621, obtained from a sensor processing stage, such as sensor processing stage 601, to one or more machine-learning units (ML), such as machine-learning units 606, for example. In an embodiment, content steering circuitry, such as content-steering circuitry 608, may direct content, such as signals and/or states 621, based, at least in part, on one or more control signals obtained from a control unit, such as control 603, and/or from a memory, such as memory 613.

In an embodiment, machine-learning units, such as machine-learning units 606, may be configured via one or more control signals, such as control signals communicated between a control unit, such as control unit 603, and machine-learning units, such as machine-learning units 606. In an embodiment, one or more machine-learning units, such as machine-learning units 606, may be configured to operate individually or in one combination with one or more other machine-learning units. In an embodiment, individual machine-learning units, such as machine-learning units 606, may implement particular machine-learning techniques. Further, one or more machine-learning units, such as machine-learning units 606, may be implemented to operate in the analog domain or in the digital domain, or a combination thereof. For example, a machine-learning unit operating in the analog domain may include voltage and/or current summing circuits to sum a number of signals and/or states and/or may include devices, such as variable impedance devices, that may apply weighting factors to individual signals and/or states. Of course, claimed subject matter is not limited in scope in these respects.

Content steering/selecting circuitry, such as content steering/selecting circuitry 607, may select and/or combine content generated by one or more machine-learning units, such as machine-learning units 606, in an embodiment. Further, content steering/selecting circuitry, such as content steering/selecting circuitry 607, may direct output, such as signals and/or states representative of behavioral profile content 625, to a decision-making system, such as decision-making system 640. In an embodiment, a control unit, such as control unit 603, may obtain at least a portion of the output generated by machine-learning units, such as machine-learning units 606.

In an embodiment, control unit, such as control unit 603, may configure and/or control one or more aspects of behavioral processing unit 600. In an embodiment, a control unit, such as control unit 603, may obtain various inputs from a variety of sources and/or may control various aspects of behavioral processing unit 600 based, at least in part, on the obtained inputs. In an embodiment, control unit inputs may be obtained from units within behavioral processing unit 600 unit itself and/or from one or more other sources. For example, control unit 603 may obtain user parameters 615 (e.g., user ID or other parameters descriptive of a particular user). In an embodiment, user parameters, such as parameters 615, may be obtained from one or more external sources and/or may be obtained from one or more memories within behavioral processing unit 600. For example, user parameters for one or more particular users may be stored in a memory, such as memory 604. Various aspects of behavioral processing unit 600 may be configured and/or reconfigured based at least in part on parameters that may be stored on an individual user basis in a memory, such as memory 604. For example, a control unit, such as control unit 603, may communicate with a memory, such as memory 604, to obtain configuration content for a particular user from memory 604, and/or may configure behavioral processing unit 600 based at least in part on the obtained configuration content. Further, in an embodiment, a control unit, such as control unit 603, may obtain content from a decision-making system, such as decision-making system 640, or from one or more external sources, such as external system 650.

Although example behavioral processing unit 600 is depicted having particular memory devices, such as memories 604, 612, 614, and/or 616, other embodiments may include memory elements distributed in various areas of the processing unit. For example, memory elements may be included in one or more sensor processing units 605 and/or in one or more machine-learning units 606. Additionally, a memory, such as memory 604, may be implemented as a hierarchy of memory devices and/or technologies that may allow for various sizes and/or memory access speeds. Further, a memory, such as memory 604, may store machine-learning weighting parameters and/or other machine-learning parameters, and/or may also store control signals, for example.

In an embodiment, a control unit, such as control unit 603, may generate one or more output signals and/or states, such as one or more control signal, based, at least in part, on inputs obtained by the control unit. Control signal output generation may be a function of one or more inputs that may include, for example, user identification parameters, content type parameters, contextual parameters, task parameters, sensor availability parameters, or behavioral profile content specification parameters, or any combination thereof. Of course, these are merely example types of inputs that may be obtained by a control unit, such as control unit 603, and claimed subject matter is not limited in scope to these particular examples.

As mentioned, a control unit, such as control unit 603, may obtain user parameters 615 that may include user identification content and/or other parameters descriptive of a particular user). Further, in an embodiment, a control unit, such as control unit 603, may obtain parameters descriptive of content being consumed by a user (e.g., music, movie, game, digital book, etc.), parameters descriptive of a task being performed by a user, or parameters descriptive of context and/or environment, or any combination thereof, for example. In an embodiment, context and/or environmental parameters 611 may be provided by and/or obtained from an external system, such as external system 650. Further, in an embodiment, content and/or task parameters 610 may be provided by and/or obtained from a decision-making system, such as decision-making system 640. For example, parameters descriptive of content type may indicate that a user is listening to and/or otherwise consuming music as opposed to participating in an interactive game. Further, for example, parameters descriptive of user/operator and/or task may indicate a type of task being performed (e.g., flying, driving, performing surgery, etc.) and/or may indicate a particular user/operator. Also, for example, parameters descriptive of context and/or environment may indicate a particular setting (e.g., location, time of day, date, etc.), presence of other individuals, or other contextual information, or any combination thereof.

A control unit, such as control unit 603, may also obtain parameters, such as parameters 614, that may be indicative of sensor availability, for example. Additionally, a control unit, such as control unit 603, may obtain parameters, such as parameters 619, that may indicate one or more particular parameters and/or parameter types of behavioral profile content, such as behavioral profile content 625, to be generated on a relative priority basis, for example, by machine-learning stage 602, for example. Further, one or more parameters 620 representative of one or more aspects of behavioral profile content 625 generated by machine-learning stage 602 may be provided to and/or obtained by a control unit, such as control unit 603. For example, parameters 620 may include feedback to control unit 603 that may influence behavioral processing unit operations, in an embodiment.

As mentioned, a control unit, such as control unit 603, may generate one or more control signals based, at least in part, on inputs that may be obtained from any of a range of sources. For example, inputs obtained by control unit 603 may allow for selecting particular content from one or more memory elements, such as one or more of memories 604, 612, 614, and/or 616, to be utilized in configuring sensor processing stage 601 and/or machine-learning stage 602 for processing. For example, sensor processing stage 601 and/or machine-learning stage 602 may be configured based on a particular user/operator, a particular task, or a particular context, or a combination thereof. By tailoring processing in this manner, improved behavioral profile content may be generated, and/or efficiency may be improved (e.g., improved confidence of behavioral profile content while utilizing relatively fewer resources). Further, in an embodiment control unit 603 may steer outputs of sensor processing stage 601 (e.g., intermediary results) to particular machine-learning units 605 via control of steering circuitry 608 based, at least in part, on inputs obtained by control unit 603. Similarly, control unit 603 may select output from one or more particular machine-learning units 606 via control of steering/selecting circuitry 607 based, at least in part, on obtained inputs. Further, weighting of inputs for machine-learning units 606 may be determined at least in part based on obtained inputs. For example, a control unit, such as control unit 603, may steer, select, and/or weight intermediary results (e.g., content generated by sensor processing stage 601) as a function of user/operator identification, content type, environmental context, or sensor availability, or any combination thereof, in an embodiment. Of course, claimed subject matter is not limited in scope in these respects.

Further, in an embodiment, resource allocation within a processor, such as behavioral processing unit 600, may be based, at least in part, on behavioral profile content specification parameters, such as parameters 619. In an embodiment, a control unit, such as control unit 603, may obtain behavioral profile content specification parameters 619 that may indicate one or more behavioral profile parameters to be relatively prioritized, for example, and may select particular sensor processing units 605 and/or particular machine-learning units 606 based, at least in part, on the specified behavioral profile content parameters. "Relatively prioritized" in the context of behavioral profile content specification parameters, such as parameters 619, refers to one or more particular parameters to be processed on a priority basis over other parameters. For example, behavioral profile content specification parameters 619 may indicate an "anger" parameter. Resources (e.g., SPUs 605, machine-learning units 606, memory, etc.) sufficient to process the "anger" parameter to a particular confidence level, for example, may be allocated, even at the expense of resources that may otherwise be allocated to generating other behavioral profile content parameters. Control unit 603 may, via one or more control signals, select resources from sensor processing stage 601 and/or machine-learning stage 602 to generate behavioral profile content in accordance with the specified parameters. In this manner, relatively prioritized content may be generated relatively more efficiently. Behavioral profile content specification parameters, such as parameters 619, may also indicate relative priorities related to trade-offs between power consumption and generation of particular behavioral profile content, in an embodiment. Further, in an embodiment, relatively prioritized content may be generated at the relative expense of other behavioral profile content. For example, behavioral profile parameters indicating anger and/or fatigue may be relatively prioritized over excitement and/or hunger parameters, and control unit 603 may configure sensor processing stage 601 and/or machine-learning stage 602 accordingly. Further, in an embodiment, self-feedback and/or output monitoring content, such as content 620, may allow for control adjustments, such as selecting additional/different machine-learning units and/or sensor processing units and/or otherwise adjusting resource utilization within behavioral processing unit 600. Such adjustments may be made, for example, to meet specified relative priorities, specified levels of confidence in generated output, etc.

Although some embodiments described herein mention neural network techniques for machine learning, subject matter is not limited in scope in this respect. Other embodiments may incorporate other machine learning techniques either presently existing or to be developed in the future. Further, for embodiments implementing neural networks, for example, sensors may be removed from a system during offline pre-deployment training operations such that a neural network may determine appropriate weights for various sensor combinations. In another embodiment, during online operation, for example, a set of input biomarkers may be logged and/or later used as training parameters, wherein a predicted behavioral processing unit output may be utilized at least in part to train one or more networks that may lack some subset of the initial inputs. For online inference, an appropriate neural network may be selected based at least in part on available sensor inputs. Such an arrangement may be advantageous in situations wherein an operator may remove one or more sensors from a system, device, and/or process. For example, during surgery, a surgeon may remove his or her glasses that may have been tracking eye movement. In an embodiment, a different neural network configuration may be selected at least in part in response to such a change in available sensor input, for example. For example, a control unit, such as control unit 603, may detect a change in sensor availability (e.g., signified by sensor availability input 614), and/or may reconfigure sensor processing units 605 and/or machine-learning units 606 based at least in part on the detected change in sensor availability.

Figure 7:
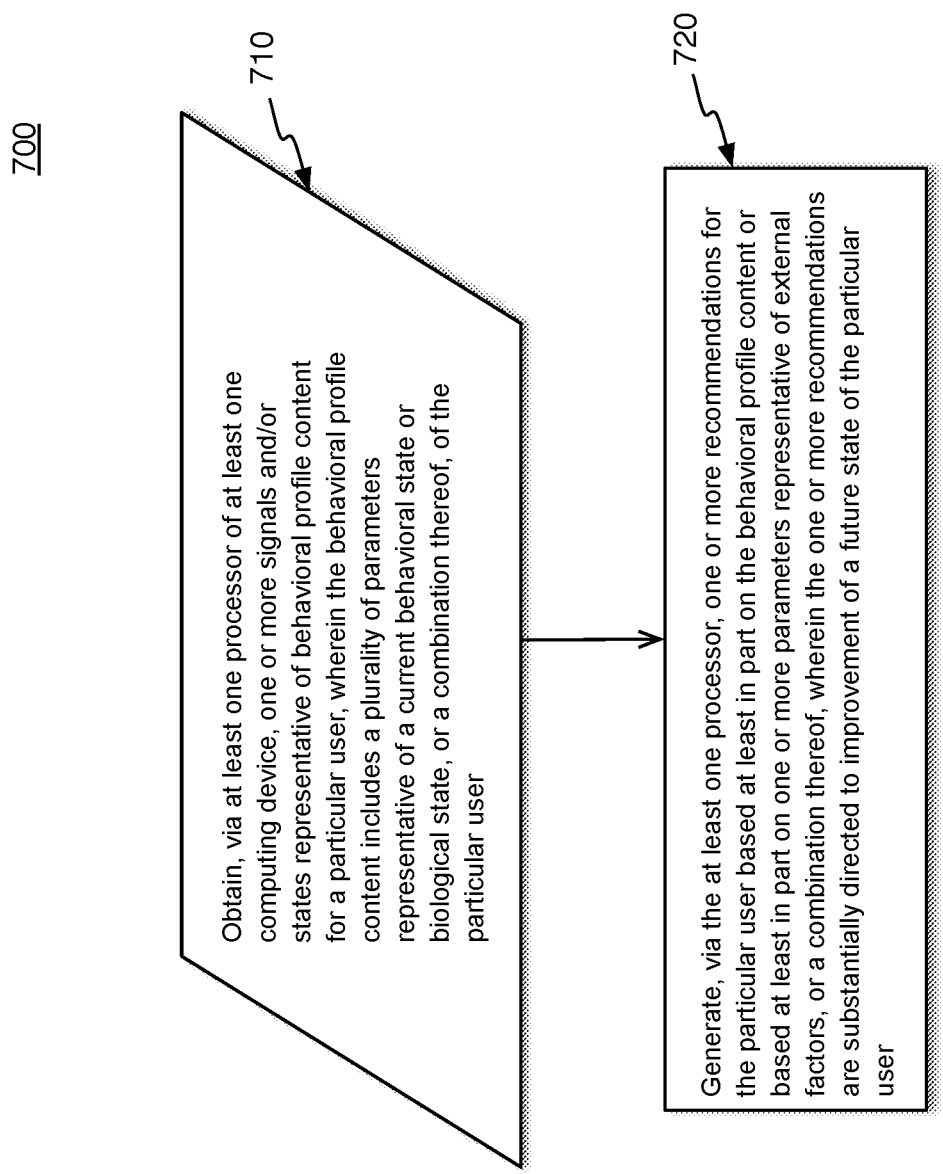
FIG. 7 is an illustration of an example process for processing signals and/or states representative of behavioral profile content, in accordance with an embodiment.

FIG. 7 is an illustration of an embodiment 700 of an example process for processing signals and/or states representative of behavioral profile content. Embodiments in accordance with claimed subject matter may include all of blocks 710-720, fewer than blocks 710-720, and/or more than blocks 710-720. Further, the order of blocks 710-720 is merely an example order, and claimed subject matter is not limited in scope in these respects.

As indicated at block 710, one or more signals and/or states representative of behavioral profile content for a particular user may be obtained via at least one processor, such as processor 110, of at least one computing device, wherein the behavioral profile content may include a plurality of parameters, such as parameters 240, representative of a substantially current behavioral state or biological state, or a combination thereof, of the particular user. Further, as indicated at 720, one or more recommendations for the particular user may be generated via at least one processor, such as processor 110, based at least in part on the behavioral profile content and/or based at least in part on one or more parameters representative of external factors, or a combination thereof, wherein the one or more recommendations may be substantially directed to improvement of a future state of the particular user. Also, as mentioned, embodiments may include generating behavioral profile content and/or recommendations intended to be communicated to one or more other individuals. For example, as discussed above, embodiments directed to collaborative mental health management, for example, may include sharing behavioral profile content and/or recommendations between personal computing devices within a group of individuals.

In an embodiment, generating one or more recommendations for the particular user may be generated at least in part by a behavioral processing unit, such as BPU 600, for example. That is, in embodiments, a behavioral processing unit, such as BPU 600, may generate behavioral profile content and/or may also perform machine learning operations on behavioral profile content and/or on one or more parameters representative of external factors to generate one or more recommendations for a particular user and/or to perform other decision-making operations.

Figure 8:
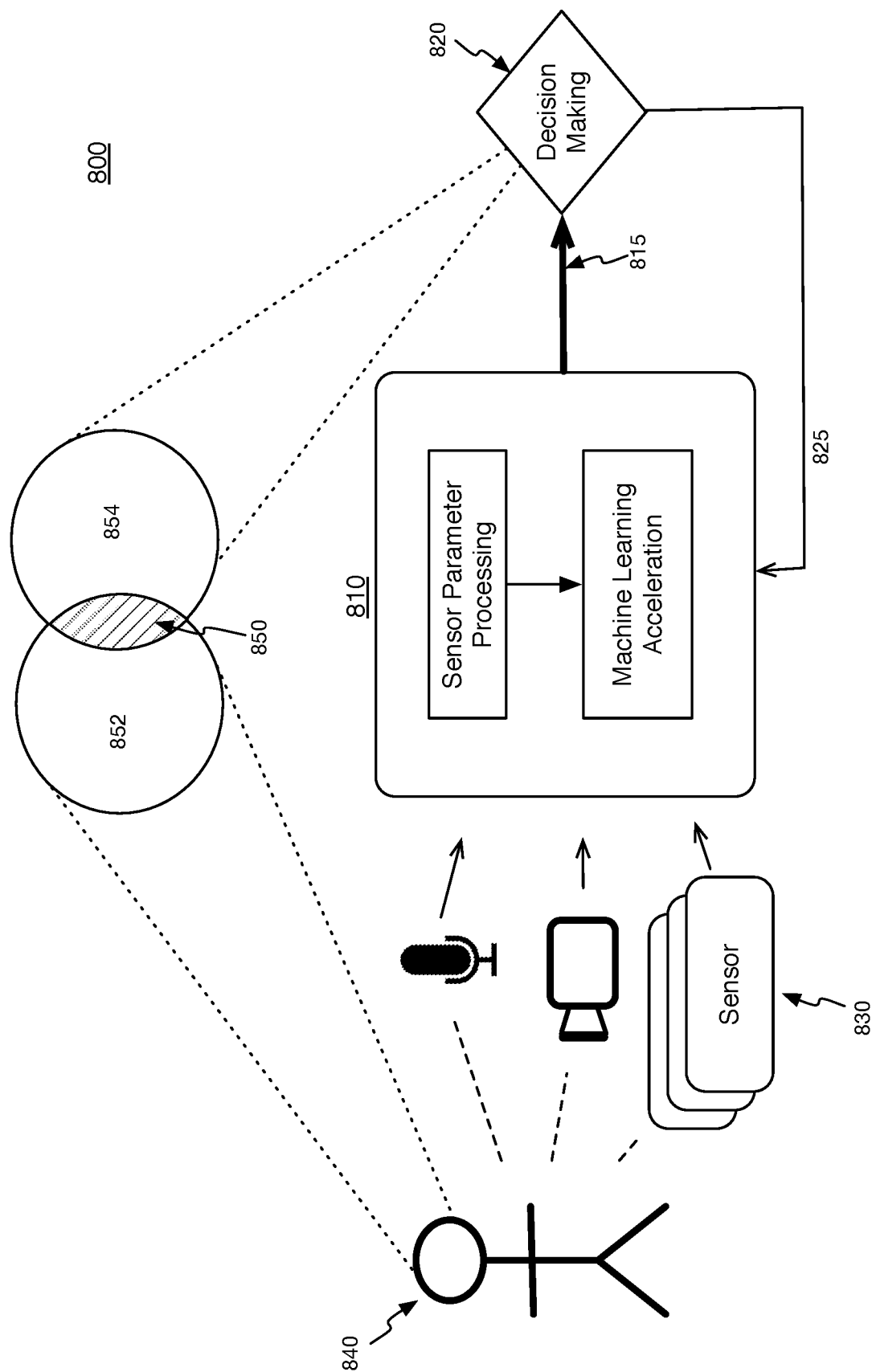
FIG. 8 is an illustration of an example device, system, and/or process for processing signals and/or states representative of behavioral content, in accordance with an embodiment.

FIG. 8 is an illustration of an embodiment 800 of an example device, system, and/or process for processing signals and/or states representative of behavioral content to shift responsibility of control of one or more aspects of a particular machine from a particular operator to an automated device, system, and/or process, for example. In some situations, a shift may occur from human-directed machines to human-machine cooperation with relatively significant decision-making performed by machines. Some machine-based decisions may depend, at least in part, on an operator's state and/or on an ability to respond substantially immediately and/or relatively quickly to changes in an operator's state. Additionally, a growing number of sensors, such as sensors 830, may be capable of generating signals and/or states representative of various aspects of an operator's biological and/or behavioral state. Embodiments, including behavioral processing unit 810, for example, may coordinate content generated by sensors, such as sensors 830, and/or may accelerate processing of sensor content to relatively quickly provide a relatively feature-rich and/or normalized state of an operator (e.g., behavioral profile parameters 815) to one or more external decision-making systems, such as decision-making system 820. In an embodiment, by consolidating and/or isolating, for example, the processing of sensor content into a specialized device, such as BPU 810, an availability of resources sufficient to determine a behavioral and/or biological state of an operator may be improved and/or ensured. Further, embodiments may provide accelerated processing of real-time biological sensor content and/or machine-learning for inferring a behavioral and/or biological state of an operator from processed sensor content, for example.

Some embodiments may be relevant to any area that may benefit from substantially real-time determination of operator state, including, for example, technology-assisted driving and/or flying in military and/or commercial scenarios. Embodiments may be particularly relevant in situations where an allocation of responsibilities may shift based at least in part on operator state. For example, to generate behavioral profile content, such as behavioral profile content 815, for a particular operator, such as operator 840, a processor, such as behavioral processing unit 810, may obtain signals and/or states representative of content from one or more sensors, such as one or more of sensors 830. Also, in an embodiment, a processor, such as behavioral processing unit 810, may process sensor content, such as content from one or more of sensors 830, to generate behavioral profile content, such as behavioral profile content 815, for a particular operator, such as operator 840.

In an embodiment, a computing device-based decision-making system, device, and/or process, such as system 820, may include machine learning and/or artificial intelligence techniques, for example. Behavioral profile content, such as behavioral profile content 815, may include a plurality of parameters representative of focal point, excitement, anger, fear, fatigue, dehydration, confusion, agitation, and/or focus/distraction, for example. In an embodiment, various aspects of behavioral profile content may individually include vectors of parameters. For example, an "anger" vector may include parameters indicating a particular state, a score related to that state, a confidence parameter, and/or a direction and/or trend parameter, in an embodiment. Also, in an embodiment, a computing device-based decision-making system, device, and/or process, such as system 820, may provide calibration and/or hint parameters, such as parameters 825, to a processor, such as behavioral processing unit 810, although, again, subject matter is not limited in scope in these respects.

Also, in an embodiment, a processor, such as behavioral processing unit 810, may repetitively and/or continuously obtain sensor content and/or may repetitively and/or continuously generate behavioral profile content for particular operators. For example, sensor content may be gathered and/or otherwise obtained at regular intervals, and/or behavioral profile content may be generated at regular intervals. In an embodiment, a computing device-based decision-making system, device, and/or process, such as system 820, may track behavioral profile content over a period of time, for example, to detect changes in behavioral profile content.

As mentioned, embodiments may include processing of signals and/or states representative of sensor content. In at least some embodiments, sensor content may comprise analog signals and/or digital signals, or a combination thereof. Further, although digital processing circuitry may be described in connection with various example embodiments, subject matter is not limited to digital implementations. For example, embodiments may implement analog circuitry for processing sensor content. Similarly, signals and/or states that may be generated to control operation of a machine, for example, may comprise digital and/or analog signals and/or states, or a combination thereof. In an embodiment, analog hysteretic "winner-take-all" circuits may be implemented at least in part to improve noise robustness and/or to mitigate, at least in part, timing difference between sensor input streams, for example. Of course, subject matter is not limited in scope in these respects.

As mentioned, embodiments may be utilized in situations that may benefit from substantially real-time determination of a biological and/or behavioral state of a particular operator, including, for example, technology-assisted driving and/or flying, such as in commercial and/or military scenarios, for example. Of course, subject matter is not limited to these particular examples. In an embodiment, responsibility for operating one or more aspects of a particular machine may shift from operator to computing device, for example, depending, at least in part, on a substantially current biological and/or behavioral state of a particular operator. For example, FIG. 8 depicts an area of responsibility, illustrated as area 854, under control of a computing device decision-making system, device, and/or process, such as 820. FIG. 8 also depicts an area of responsibility, illustrated as area 852, under control of a particular operator, such as operator 840. Area 850, also depicted in FIG. 8, illustrates an area of shared responsibility between a computing device-based decision-making system, device, and/or process, such as 820, and operator-based control, such as by operator 840. In an embodiment, whether a particular operator, such as operator 840, and/or a computing device-based decision-making system, device, and/or process, such as system 820, performs tasks illustrated by area 850 may depend, at least in part, on a substantially current biological and/or behavioral state of the particular operator. In an embodiment, such a determination may be made, at least in part, by a computing device-based decision-making system, device, and/or process, such as system 820, based at least in part on behavioral profile content, such as behavioral profile content 815, obtained from a processor, such as behavioral processing unit 810, for example.

Returning to an example of an operator, such as a pilot, flying an aircraft, the operator may control some aspects of the aircraft while a computing device-based decision-making system, device, and/or process, such as system 820, controls other aspects of the aircraft. For the current example, an area of variable responsibility, such as area of variable responsibility 850, may represent one or more aspects of aircraft operation that may be shifted at least in part from pilot control to computing device control depending at least in part on a substantially current biological and/or behavioral state of the pilot. For example, if a processor, such as behavioral processing unit 810, detects at least in part via sensor content that the pilot is fatigued, agitated, angry, etc. beyond specified thresholds, for example, responsibility and/or operation of flight controls (e.g., rudder, elevators, etc.) may be shifted from pilot control to control by computing device-based decision-making system, device, and/or process, such as system 820.

In another example, shared responsibility area 850 may represent an automobile braking system that may, under normal conditions, be under at least partial control of a particular operator. At least in part in response to a processor, such as behavior processing unit 810, generating behavioral profile content for a particular operator that indicates a change in a substantially current biological and/or behavioral state for the particular operator that may indicate a dangerous condition for the operator and/or for others, a computing device-based decision-making system, device, and/or process, such as system 820, may assume control of the braking system. Of course, subject matter is not limited to these particular examples.

In a further example, anesthesia during a surgical procedure may be administered to a patient in accordance with a computing device-based decision-making system, device, and/or process, such as system 820. In an embodiment, a surgeon may comprise an "operator" in that the surgeon may be monitored via one or more sensors. Administration of anesthesia may be initially based, at least in part, on an expected duration of the surgical procedure. A processor, such as behavioral processing unit 810, may generate behavioral profile content for the surgeon, and a computing device-based decision-making system, device, and/or process, such as system 820, may determine whether administration of anesthesia should be altered based at least in part on a current biological and/or behavioral state of the surgeon. For example, behavioral profile content may indicate an increase is stress levels being experienced by the surgeon, and/or may indicate an acknowledgement by the surgeon of an error during the procedure. A computing device-based decision-making system, device, and/or process, such as system 820, may determine to alter administration of anesthesia based on an anticipated increase in expected duration of the surgical procedure due at least in part to the increased stress levels and/or detected error acknowledgement, for example.

In another example involving a surgical procedure, a surgeon may utilize a robotic surgical device that may be used manually, that may operate autonomously, and/or that may share operational aspects between the robotic surgical device and the surgeon (e.g., a machine-assisted mode of operation). In an embodiment, at least one processor, such as system 820, may initiate control of one or more aspects of a surgical intervention to at least partially shift control of the surgical intervention from the surgeon to the robotic surgical device based, at least in part, on behavioral profile content.

For another example, a law enforcement officer may carry one or more weapons. A processor, such as behavioral processing unit 810, may generate behavioral profile content for the law enforcement officer, and a computing device-based decision-making system, device, and/or process, such as system 820, may determine whether aspects of functionality with respect to the officer's weapon should be altered based at least in part on a current biological and/or behavioral state of the officer. For example, behavioral profile content may indicate an increase in anger levels being experienced by the officer, and/or may indicate a degree of impairment of some kind on the part of the officer. A computing device-based decision-making system, device, and/or process, such as system 820, may determine to latch a safety on the weapon, for example, to prevent the use of the weapon. Alternatively, for example, behavioral profile content may provide an indication to a decision-making system, device, and/or process, such as system 820, to provide additional help in aiming the weapon. For example, the weapon may be transitioned from a manual-aim mode to an assisted-aim mode based at least in part on behavioral profile content.

In the context of the present patent application, the term "connection," the term "component" and/or similar terms are intended to be physical, but are not necessarily always tangible. Whether or not these terms refer to tangible subject matter, thus, may vary in a particular context of usage. As an example, a tangible connection and/or tangible connection path may be made, such as by a tangible, electrical connection, such as an electrically conductive path comprising metal or other conductor, that is able to conduct electrical current between two tangible components. Likewise, a tangible connection path may be at least partially affected and/or controlled, such that, as is typical, a tangible connection path may be open or closed, at times resulting from influence of one or more externally derived signals, such as external currents and/or voltages, such as for an electrical switch. Non-limiting illustrations of an electrical switch include a transistor, a diode, etc. However, a "connection" and/or "component," in a particular context of usage, likewise, although physical, can also be non-tangible, such as a connection between a client and a server over a network, which generally refers to the ability for the client and server to transmit, receive, and/or exchange communications, as discussed in more detail later. Also, the term "connection" may be utilized in a context of a neural network model, and may, in an embodiment, refer to parameters passed between nodes that may include parameters and/or sets of parameters representative of output values, for example. Also, in an embodiment, connections between nodes may include weight parameters. For example, one or more weight parameters may operate in a specified manner on one or more parameters representative of one or more output values to yield a connection, such as between a node of a first layer and a node of a second layer, in an embodiment, for example.

In a particular context of usage, such as a particular context in which tangible components are being discussed, therefore, the terms "coupled" and "connected" are used in a manner so that the terms are not synonymous. Similar terms may also be used in a manner in which a similar intention is exhibited. Thus, "connected" is used to indicate that two or more tangible components and/or the like, for example, are tangibly in direct physical contact. Thus, using the previous example, two tangible components that are electrically connected are physically connected via a tangible electrical connection, as previously discussed. However, "coupled," is used to mean that potentially two or more tangible components are tangibly in direct physical contact. Nonetheless, is also used to mean that two or more tangible components and/or the like are not necessarily tangibly in direct physical contact, but are able to co-operate, liaise, and/or interact, such as, for example, by being "optically coupled." Likewise, the term "coupled" is also understood to mean indirectly connected. It is further noted, in the context of the present patent application, since memory, such as a memory component and/or memory states, is intended to be non-transitory, the term physical, at least if used in relation to memory necessarily implies that such memory components and/or memory states, continuing with the example, are tangible.

Additionally, in the present patent application, in a particular context of usage, such as a situation in which tangible components (and/or similarly, tangible materials) are being discussed, a distinction exists between being "on" and being "over." As an example, deposition of a substance "on" a substrate refers to a deposition involving direct physical and tangible contact without an intermediary, such as an intermediary substance, between the substance deposited and the substrate in this latter example; nonetheless, deposition "over" a substrate, while understood to potentially include deposition "on" a substrate (since being "on" may also accurately be described as being "over"), is understood to include a situation in which one or more intermediaries, such as one or more intermediary substances, are present between the substance deposited and the substrate so that the substance deposited is not necessarily in direct physical and tangible contact with the substrate.

A similar distinction is made in an appropriate particular context of usage, such as in which tangible materials and/or tangible components are discussed, between being "beneath" and being "under." While "beneath," in such a particular context of usage, is intended to necessarily imply physical and tangible contact (similar to "on," as just described), "under" potentially includes a situation in which there is direct physical and tangible contact, but does not necessarily imply direct physical and tangible contact, such as if one or more intermediaries, such as one or more intermediary substances, are present. Thus, "on" is understood to mean "immediately over" and "beneath" is understood to mean "immediately under."

It is likewise appreciated that terms such as "over" and "under" are understood in a similar manner as the terms "up," "down," "top," "bottom," and so on, previously mentioned. These terms may be used to facilitate discussion, but are not intended to necessarily restrict scope of claimed subject matter. For example, the term "over," as an example, is not meant to suggest that claim scope is limited to only situations in which an embodiment is right side up, such as in comparison with the embodiment being upside down, for example. An example includes a flip chip, as one illustration, in which, for example, orientation at various times (e.g., during fabrication) may not necessarily correspond to orientation of a final product. Thus, if an object, as an example, is within applicable claim scope in a particular orientation, such as upside down, as one example, likewise, it is intended that the latter also be interpreted to be included within applicable claim scope in another orientation, such as right side up, again, as an example, and vice-versa, even if applicable literal claim language has the potential to be interpreted otherwise. Of course, again, as always has been the case in the specification of a patent application, particular context of description and/or usage provides helpful guidance regarding reasonable inferences to be drawn.

Unless otherwise indicated, in the context of the present patent application, the term "or" if used to associate a list, such as A, B, or C, is intended to mean A, B, and C, here used in the inclusive sense, as well as A, B, or C, here used in the exclusive sense. With this understanding, "and" is used in the inclusive sense and intended to mean A, B, and C; whereas "and/or" can be used in an abundance of caution to make clear that all of the foregoing meanings are intended, although such usage is not required. In addition, the term "one or more" and/or similar terms is used to describe any feature, structure, characteristic, and/or the like in the singular, "and/or" is also used to describe a plurality and/or some other combination of features, structures, characteristics, and/or the like. Likewise, the term "based on" and/or similar terms are understood as not necessarily intending to convey an exhaustive list of factors, but to allow for existence of additional factors not necessarily expressly described.

Furthermore, it is intended, for a situation that relates to implementation of claimed subject matter and is subject to testing, measurement, and/or specification regarding degree, to be understood in the following manner. As an example, in a given situation, assume a value of a physical property is to be measured. If alternatively reasonable approaches to testing, measurement, and/or specification regarding degree, at least with respect to the property, continuing with the example, is reasonably likely to occur to one of ordinary skill, at least for implementation purposes, claimed subject matter is intended to cover those alternatively reasonable approaches unless otherwise expressly indicated. As an example, if a plot of measurements over a region is produced and implementation of claimed subject matter refers to employing a measurement of slope over the region, but a variety of reasonable and alternative techniques to estimate the slope over that region exist, claimed subject matter is intended to cover those reasonable alternative techniques unless otherwise expressly indicated.

To the extent claimed subject matter is related to one or more particular measurements, such as with regard to physical manifestations capable of being measured physically, such as, without limit, temperature, pressure, voltage, current, electromagnetic radiation, etc., it is believed that claimed subject matter does not fall with the abstract idea judicial exception to statutory subject matter. Rather, it is asserted, that physical measurements are not mental steps and, likewise, are not abstract ideas.

It is noted, nonetheless, that a typical measurement model employed is that one or more measurements may respectively comprise a sum of at least two components. Thus, for a given measurement, for example, one component may comprise a deterministic component, which in an ideal sense, may comprise a physical value (e.g., sought via one or more measurements), often in the form of one or more signals, signal samples and/or states, and one component may comprise a random component, which may have a variety of sources that may be challenging to quantify. At times, for example, lack of measurement precision may affect a given measurement. Thus, for claimed subject matter, a statistical or stochastic model may be used in addition to a deterministic model as an approach to identification and/or prediction regarding one or more measurement values that may relate to claimed subject matter.

For example, a relatively large number of measurements may be collected to better estimate a deterministic component. Likewise, if measurements vary, which may typically occur, it may be that some portion of a variance may be explained as a deterministic component, while some portion of a variance may be explained as a random component. Typically, it is desirable to have stochastic variance associated with measurements be relatively small, if feasible. That is, typically, it may be preferable to be able to account for a reasonable portion of measurement variation in a deterministic manner, rather than a stochastic matter as an aid to identification and/or predictability.

Along these lines, a variety of techniques have come into use so that one or more measurements may be processed to better estimate an underlying deterministic component, as well as to estimate potentially random components. These techniques, of course, may vary with details surrounding a given situation. Typically, however, more complex problems may involve use of more complex techniques. In this regard, as alluded to above, one or more measurements of physical manifestations may be modeled deterministically and/or stochastically. Employing a model permits collected measurements to potentially be identified and/or processed, and/or potentially permits estimation and/or prediction of an underlying deterministic component, for example, with respect to later measurements to be taken. A given estimate may not be a perfect estimate; however, in general, it is expected that on average one or more estimates may better reflect an underlying deterministic component, for example, if random components that may be included in one or more obtained measurements, are considered. Practically speaking, of course, it is desirable to be able to generate, such as through estimation approaches, a physically meaningful model of processes affecting measurements to be taken.

In some situations, however, as indicated, potential influences may be complex. Therefore, seeking to understand appropriate factors to consider may be particularly challenging. In such situations, it is, therefore, not unusual to employ heuristics with respect to generating one or more estimates. Heuristics refers to use of experience related approaches that may reflect realized processes and/or realized results, such as with respect to use of historical measurements, for example. Heuristics, for example, may be employed in situations where more analytical approaches may be overly complex and/or nearly intractable. Thus, regarding claimed subject matter, an innovative feature may include, in an example embodiment, heuristics that may be employed, for example, to estimate and/or predict one or more measurements.

It is further noted that the terms "type" and/or "like," if used, such as with a feature, structure, characteristic, and/or the like, using "optical" or "electrical" as simple examples, means at least partially of and/or relating to the feature, structure, characteristic, and/or the like in such a way that presence of minor variations, even variations that might otherwise not be considered fully consistent with the feature, structure, characteristic, and/or the like, do not in general prevent the feature, structure, characteristic, and/or the like from being of a "type" and/or being "like," (such as being an "optical-type" or being "optical-like," for example) if the minor variations are sufficiently minor so that the feature, structure, characteristic, and/or the like would still be considered to be substantially present with such variations also present. Thus, continuing with this example, the terms optical-type and/or optical-like properties are necessarily intended to include optical properties. Likewise, the terms electrical-type and/or electrical-like properties, as another example, are necessarily intended to include electrical properties. It should be noted that the specification of the present patent application merely provides one or more illustrative examples and claimed subject matter is intended to not be limited to one or more illustrative examples; however, again, as has always been the case with respect to the specification of a patent application, particular context of description and/or usage provides helpful guidance regarding reasonable inferences to be drawn.

In the context of the present patent application, the term network device refers to any device capable of communicating via and/or as part of a network and may comprise a computing device. While network devices may be capable of communicating signals (e.g., signal packets and/or frames), such as via a wired and/or wireless network, they may also be capable of performing operations associated with a computing device, such as arithmetic and/or logic operations, processing and/or storing operations (e.g., storing signal samples), such as in memory as tangible, physical memory states, and/or may, for example, operate as a server device and/or a client device in various embodiments. Network devices capable of operating as a server device, a client device and/or otherwise, may include, as examples, dedicated rack-mounted servers, desktop computers, laptop computers, set top boxes, tablets, netbooks, smart phones, wearable devices, integrated devices combining two or more features of the foregoing devices, and/or the like, or any combination thereof. As mentioned, signal packets and/or frames, for example, may be exchanged, such as between a server device and/or a client device, as well as other types of devices, including between wired and/or wireless devices coupled via a wired and/or wireless network, for example, or any combination thereof. It is noted that the terms, server, server device, server computing device, server computing platform and/or similar terms are used interchangeably. Similarly, the terms client, client device, client computing device, client computing platform and/or similar terms are also used interchangeably. While in some instances, for ease of description, these terms may be used in the singular, such as by referring to a "client device" or a "server device," the description is intended to encompass one or more client devices and/or one or more server devices, as appropriate. Along similar lines, references to a "database" are understood to mean, one or more databases and/or portions thereof, as appropriate.

It should be understood that for ease of description, a network device (also referred to as a networking device) may be embodied and/or described in terms of a computing device and vice-versa. However, it should further be understood that this description should in no way be construed so that claimed subject matter is limited to one embodiment, such as only a computing device and/or only a network device, but, instead, may be embodied as a variety of devices or combinations thereof, including, for example, one or more illustrative examples.

A network may also include now known, and/or to be later developed arrangements, derivatives, and/or improvements, including, for example, past, present and/or future mass storage, such as network attached storage (NAS), a storage area network (SAN), and/or other forms of device readable media, for example. A network may include a portion of the Internet, one or more local area networks (LANs), one or more wide area networks (WANs), wire-line type connections, wireless type connections, other connections, or any combination thereof. Thus, a network may be worldwide in scope and/or extent. Likewise, sub-networks, such as may employ differing architectures and/or may be substantially compliant and/or substantially compatible with differing protocols, such as network computing and/or communications protocols (e.g., network protocols), may interoperate within a larger network.

The term electronic file and/or the term electronic document are used throughout this document to refer to a set of stored memory states and/or a set of physical signals associated in a manner so as to thereby at least logically form a file (e.g., electronic) and/or an electronic document. That is, it is not meant to implicitly reference a particular syntax, format and/or approach used, for example, with respect to a set of associated memory states and/or a set of associated physical signals. If a particular type of file storage format and/or syntax, for example, is intended, it is referenced expressly. It is further noted an association of memory states, for example, may be in a logical sense and not necessarily in a tangible, physical sense. Thus, although signal and/or state components of a file and/or an electronic document, for example, are to be associated logically, storage thereof, for example, may reside in one or more different places in a tangible, physical memory, in an embodiment.

In the context of the present patent application, the terms "entry," "electronic entry," "document," "electronic document," "content,", "digital content," "item," and/or similar terms are meant to refer to signals and/or states in a physical format, such as a digital signal and/or digital state format, e.g., that may be perceived by a user if displayed, played, tactilely generated, etc. and/or otherwise executed by a device, such as a digital device, including, for example, a computing device, but otherwise might not necessarily be readily perceivable by humans (e.g., if in a digital format). Likewise, in the context of the present patent application, digital content provided to a user in a form so that the user is able to readily perceive the underlying content itself (e.g., content presented in a form consumable by a human, such as hearing audio, feeling tactile sensations and/or seeing images, as examples) is referred to, with respect to the user, as "consuming" digital content, "consumption" of digital content, "consumable" digital content and/or similar terms. For one or more embodiments, an electronic document and/or an electronic file may comprise a Web page of code (e.g., computer instructions) in a markup language executed or to be executed by a computing and/or networking device, for example. In another embodiment, an electronic document and/or electronic file may comprise a portion and/or a region of a Web page. However, claimed subject matter is not intended to be limited in these respects.

Also, for one or more embodiments, an electronic document and/or electronic file may comprise a number of components. As previously indicated, in the context of the present patent application, a component is physical, but is not necessarily tangible. As an example, components with reference to an electronic document and/or electronic file, in one or more embodiments, may comprise text, for example, in the form of physical signals and/or physical states (e.g., capable of being physically displayed). Typically, memory states, for example, comprise tangible components, whereas physical signals are not necessarily tangible, although signals may become (e.g., be made) tangible, such as if appearing on a tangible display, for example, as is not uncommon. Also, for one or more embodiments, components with reference to an electronic document and/or electronic file may comprise a graphical object, such as, for example, an image, such as a digital image, and/or sub-objects, including attributes thereof, which, again, comprise physical signals and/or physical states (e.g., capable of being tangibly displayed). In an embodiment, digital content may comprise, for example, text, images, audio, video, and/or other types of electronic documents and/or electronic files, including portions thereof, for example.

Also, in the context of the present patent application, the term parameters (e.g., one or more parameters) refer to material descriptive of a collection of signal samples, such as one or more electronic documents and/or electronic files, and exist in the form of physical signals and/or physical states, such as memory states. For example, one or more parameters, such as referring to an electronic document and/or an electronic file comprising an image, may include, as examples, time of day at which an image was captured, latitude and longitude of an image capture device, such as a camera, for example, etc. In another example, one or more parameters relevant to digital content, such as digital content comprising a technical article, as an example, may include one or more authors, for example. Claimed subject matter is intended to embrace meaningful, descriptive parameters in any format, so long as the one or more parameters comprise physical signals and/or states, which may include, as parameter examples, collection name (e.g., electronic file and/or electronic document identifier name), technique of creation, purpose of creation, time and date of creation, logical path if stored, coding formats (e.g., type of computer instructions, such as a markup language) and/or standards and/or specifications used so as to be protocol compliant (e.g., meaning substantially compliant and/or substantially compatible) for one or more uses, and so forth.

Signal packet communications and/or signal frame communications, also referred to as signal packet transmissions and/or signal frame transmissions (or merely "signal packets" or "signal frames"), may be communicated between nodes of a network, where a node may comprise one or more network devices and/or one or more computing devices, for example. As an illustrative example, but without limitation, a node may comprise one or more sites employing a local network address, such as in a local network address space. Likewise, a device, such as a network device and/or a computing device, may be associated with that node. It is also noted that in the context of this patent application, the term "transmission" is intended as another term for a type of signal communication that may occur in any one of a variety of situations. Thus, it is not intended to imply a particular directionality of communication and/or a particular initiating end of a communication path for the "transmission" communication. For example, the mere use of the term in and of itself is not intended, in the context of the present patent application, to have particular implications with respect to the one or more signals being communicated, such as, for example, whether the signals are being communicated "to" a particular device, whether the signals are being communicated "from" a particular device, and/or regarding which end of a communication path may be initiating communication, such as, for example, in a "push type" of signal transfer or in a "pull type" of signal transfer. In the context of the present patent application, push and/or pull type signal transfers are distinguished by which end of a communications path initiates signal transfer.

Thus, a signal packet and/or frame may, as an example, be communicated via a communication channel and/or a communication path, such as comprising a portion of the Internet and/or the Web, from a site via an access node coupled to the Internet or vice-versa. Likewise, a signal packet and/or frame may be forwarded via network nodes to a target site coupled to a local network, for example. A signal packet and/or frame communicated via the Internet and/or the Web, for example, may be routed via a path, such as either being "pushed" or "pulled," comprising one or more gateways, servers, etc. that may, for example, route a signal packet and/or frame, such as, for example, substantially in accordance with a target and/or destination address and availability of a network path of network nodes to the target and/or destination address. Although the Internet and/or the Web comprise a network of interoperable networks, not all of those interoperable networks are necessarily available and/or accessible to the public.

In the context of the particular patent application, a network protocol, such as for communicating between devices of a network, may be characterized, at least in part, substantially in accordance with a layered description, such as the so-called Open Systems Interconnection (OSI) seven layer type of approach and/or description. A network computing and/or communications protocol (also referred to as a network protocol) refers to a set of signaling conventions, such as for communication transmissions, for example, as may take place between and/or among devices in a network. In the context of the present patent application, the term "between" and/or similar terms are understood to include "among" if appropriate for the particular usage and vice-versa. Likewise, in the context of the present patent application, the terms "compatible with," "comply with" and/or similar terms are understood to respectively include substantial compatibility and/or substantial compliance.

A network protocol, such as protocols characterized substantially in accordance with the aforementioned OSI description, has several layers. These layers are referred to as a network stack. Various types of communications (e.g., transmissions), such as network communications, may occur across various layers. A lowest level layer in a network stack, such as the so-called physical layer, may characterize how symbols (e.g., bits and/or bytes) are communicated as one or more signals (and/or signal samples) via a physical medium (e.g., twisted pair copper wire, coaxial cable, fiber optic cable, wireless air interface, combinations thereof, etc.). Progressing to higher-level layers in a network protocol stack, additional operations and/or features may be available via engaging in communications that are substantially compatible and/or substantially compliant with a particular network protocol at these higher-level layers. For example, higher-level layers of a network protocol may, for example, affect device permissions, user permissions, etc.

A network and/or sub-network, in an embodiment, may communicate via signal packets and/or signal frames, such via participating digital devices and may be substantially compliant and/or substantially compatible with, but is not limited to, now known and/or to be developed, versions of any of the following network protocol stacks: ARCNET, AppleTalk, ATM, Bluetooth, DECnet, Ethernet, FDDI, Frame Relay, HIPPI, IEEE 1394, IEEE 802.11, IEEE-488, Internet Protocol Suite, IPX, Myrinet, OSI Protocol Suite, QsNet, RS-232, SPX, System Network Architecture, Token Ring, USB, and/or X.25. A network and/or sub-network may employ, for example, a version, now known and/or later to be developed, of the following: TCP/IP, UDP, DECnet, NetBEUI, IPX, AppleTalk and/or the like. Versions of the Internet Protocol (IP) may include IPv4, IPv6, and/or other later to be developed versions.

Regarding aspects related to a network, including a communications and/or computing network, a wireless network may couple devices, including client devices, with the network. A wireless network may employ stand-alone, ad-hoc networks, mesh networks, Wireless LAN (WLAN) networks, cellular networks, and/or the like. A wireless network may further include a system of terminals, gateways, routers, and/or the like coupled by wireless radio links, and/or the like, which may move freely, randomly and/or organize themselves arbitrarily, such that network topology may change, at times even rapidly. A wireless network may further employ a plurality of network access technologies, including a version of Long Term Evolution (LTE), WLAN, Wireless Router (WR) mesh, 2nd, 3rd, or 4th generation (2G, 3G, or 4G) cellular technology and/or the like, whether currently known and/or to be later developed. Network access technologies may enable wide area coverage for devices, such as computing devices and/or network devices, with varying degrees of mobility, for example.

A network may enable radio frequency and/or other wireless type communications via a wireless network access technology and/or air interface, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, ultra-wideband (UWB), 802.11b/g/n, and/or the like. A wireless network may include virtually any type of now known and/or to be developed wireless communication mechanism and/or wireless communications protocol by which signals may be communicated between devices, between networks, within a network, and/or the like, including the foregoing, of course.

Figure 9:
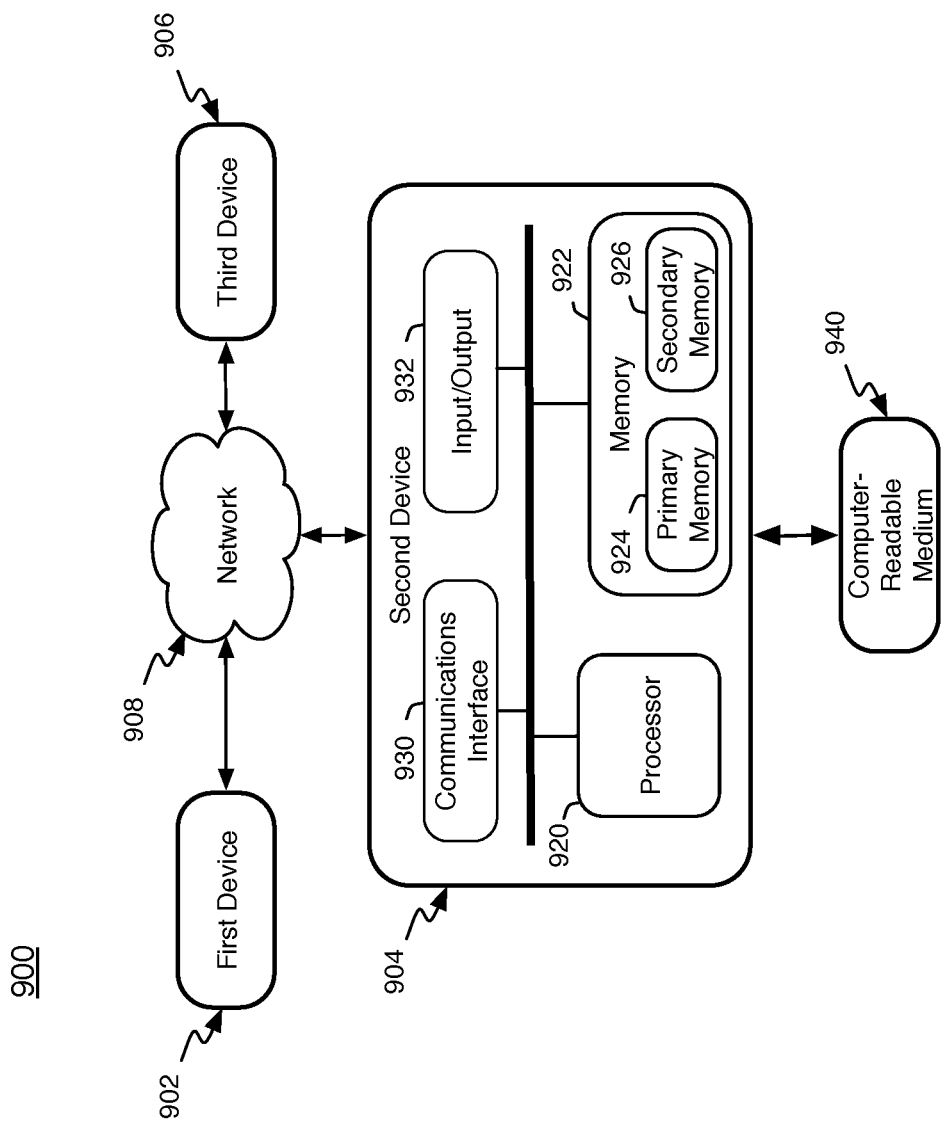
FIG. 9 is a schematic block diagram of an example computing device, in accordance with an embodiment.

In one example embodiment, as shown in FIG. 9, a system embodiment may comprise a local network (e.g., device 904 and medium 940) and/or another type of network, such as a computing and/or communications network. For purposes of illustration, therefore, FIG. 9 shows an embodiment 900 of a system that may be employed to implement either type or both types of networks. Network 908 may comprise one or more network connections, links, processes, services, applications, and/or resources to facilitate and/or support communications, such as an exchange of communication signals, for example, between a computing device, such as 902, and another computing device, such as 906, which may, for example, comprise one or more client computing devices and/or one or more server computing device. By way of example, but not limitation, network 908 may comprise wireless and/or wired communication links, telephone and/or telecommunications systems, Wi-Fi networks, Wi-MAX networks, the Internet, a local area network (LAN), a wide area network (WAN), or any combinations thereof.

Example devices in FIG. 9 may comprise features, for example, of a client computing device and/or a server computing device, in an embodiment. It is further noted that the term computing device, in general, whether employed as a client and/or as a server, or otherwise, refers at least to a processor and a memory connected by a communication bus. Likewise, in the context of the present patent application at least, this is understood to refer to sufficient structure within the meaning of 35 USC § 112 (f) so that it is specifically intended that 35 USC § 112 (f) not be implicated by use of the term "computing device" and/or similar terms; however, if it is determined, for some reason not immediately apparent, that the foregoing understanding cannot stand and that 35 USC § 112 (f), therefore, necessarily is implicated by the use of the term "computing device" and/or similar terms, then, it is intended, pursuant to that statutory section, that corresponding structure, material and/or acts for performing one or more functions be understood and be interpreted to be described at least in FIGS. 1-8, for example, and in the text associated with the foregoing figure(s) of the present patent application.

An embodiment in accordance with claimed subject matter may include a method of executing computer instructions on at least one computing device without further human interaction in which the at least one computing device includes at least one processor and at least one memory. An embodiment may include fetching computer instructions from the at least one memory of the at least one computing device for execution on the at least one processor of the at least one computing device, executing the fetched computer instructions on the at least one processor of the at least one computing device, and storing in the at least one memory of the at least one computing device any results of having executed the fetched computer instructions on the at least one processor of the at least one computing device. In an embodiment, the computer instructions to be executed comprise instructions for processing content representative of a behavioral and/or biological state of a particular user, wherein executing the fetched instructions further includes obtaining, via the at least one processor of at the least one computing device, one or more signals and/or states representative of behavioral profile content for the particular user, wherein the behavioral profile content includes a plurality of parameters representative of a current behavioral state or biological state, or a combination thereof, of the particular user, and generating, via the at least one processor, one or more recommendations for the particular user based at least in part on the behavioral profile content or based at least in part on one or more parameters representative of external factors, or a combination thereof, wherein the one or more recommendations are substantially directed to improvement of a future state of the particular user.

Further, in an embodiment, obtaining the one or more signals and/or states representative of the behavioral profile content may include repetitively obtaining updated behavioral profile content. For example, updated behavioral profile content may be obtained periodically and/or at specified intervals, in an embodiment.

In an embodiment, behavioral profile content for the particular user may include, for example, a plurality of parameters representative of focal point, excitement, anger, fear, fatigue, dehydration, focus/distraction, pre-breakthrough, silent like, regret/error acknowledgment, hunger, sloppiness/precision, empathy, or social engagement level, or any combination thereof, although claimed subject matter is not limited in scope in this respect. Further, one or more parameters representative of external factors may include one or more parameters representative of location, time of day, presence and/or identity of external individual, or general sentiment, or a combination thereof, for example.

In an embodiment, generating one or more recommendations may include performing, via at least one processor, one or more machine learning operations to determine one or more correlations between external factors and/or behavioral profile content. Also, in an embodiment, one or more parameters representative of external factors may include one or more parameters representative of content currently consumed by a particular user. Additionally, for example, performing one or more machine learning operations may determine one or more correlations between content currently consumed by a particular user and behavioral profile content to identify a silent like for a particular user.

In an embodiment, one or more parameters representative of external factors may include one or more parameters representative of content currently consumed by a particular user, and/or performing one or more machine learning operations may determine one or more correlations between content currently consumed by a particular user and behavioral profile content to select subsequent content to present to the particular user. Further, one or more parameters representative of external factors may include one or more parameters representative of content currently consumed by a particular user, and/or generating one or more recommendations for a particular user may include performing one or more machine learning operations to determine one or more correlations between content currently consumed by a particular user and behavioral profile content, wherein one or more recommendations for a particular user may include one or more actions related to dehydration, hunger, or fatigue, or a combination thereof.

In an embodiment, an apparatus may include at least one computing device, the at least one computing device including at least one processor and at least one memory, the at least one computing device to execute computer instructions on the at least one processor without further human intervention. In an embodiment, the computer instructions to be executed may be fetched from the at least one memory for execution on the at least one processor, and the at least one computing device may store in the at least one memory of the at least one computing device any results to be generated from the execution on the at least one processor of the to be executed computer instructions. In an embodiment, the computer instructions to be executed may include instructions to process content representative of a behavioral and/or biological state of a particular user. In an embodiment, the at least one processor may obtain signals and/or states representative of behavioral profile content for a particular user, the behavioral profile content to include a plurality of parameters representative of a current behavioral state or biological state, or a combination thereof, of the particular user. Further, in an embodiment, at least one memory may store signals and/or states representative of behavioral content, and/or at least one processor may generate one or more recommendations for a particular user based at least in part on behavioral profile content and/or based at least in part on one or more parameters representative of external factors, and/or a combination thereof, the one or more recommendations to be directed to improvement of a future state of the particular user.

In an embodiment, at least one processor may obtain behavioral profile content for a particular user at least in part from a behavioral content processor. Further, in an embodiment, at least one processor may repetitively obtain updated behavioral profile content. For example, a processor may obtain updated behavioral profile content periodically, and/or at specified intervals. Additionally, in an embodiment, behavioral profile content for a particular user may include a plurality of parameters representative of focal point, excitement, anger, fear, fatigue, dehydration, or focus/distraction, and/or any combination thereof, for example. In an embodiment, behavioral profile content for a particular user may further include, for example, one or more parameters representative of pre-breakthrough, silent like, regret/error acknowledgment, hunger, sloppiness/precision, empathy, or social engagement level, or any combination thereof.

In an embodiment, one or more parameters representative of external factors may comprise one or more parameters representative of location, time of day, presence and/or identity of external individual, or general sentiment, or a combination thereof, for example. Further, at least one processor may perform one or more machine learning operations to determine one or more correlations between external factors and/or the behavioral profile content, for example. In an embodiment, at least one processor may generate one or more recommendations for a particular user based at least in part on the one or more determined correlations between external factors and/or behavioral profile content. Further, in an embodiment, one or more parameters representative of external factors may include one or more parameters representative of content to be consumed by a particular user, and/or at least one processor may perform one or more machine learning operations to determine one or more correlations between content to be consumed by a particular user and/or behavioral profile content to identify a silent like for a particular user.

In an embodiment, one or more parameters representative of the external factors may include one or more parameters representative of content to be consumed by the particular user, and/or at least one processor may perform one or more machine learning operations to determine one or more correlations between content to be consumed by a particular user and behavioral profile content to select subsequent content to be presented to a particular user. Further, in an embodiment, one or more parameters representative of external factors may include, for example, one or more parameters representative of content to be consumed by the particular user, and/or, to generate the one or more recommendations for the particular user, at least one processor may perform one or more machine learning operations to determine one or more correlations between content to be consumed by a particular user and behavioral profile content, wherein one or more recommendations for a particular user may include one or more actions related to dehydration, hunger, or fatigue, or a combination thereof.

Referring now again to FIG. 9, in an embodiment, first and third devices 902 and 906 may be capable of rendering a graphical user interface (GUI) for a network device and/or a computing device, for example, so that a user-operator may engage in system use. Device 904 may potentially serve a similar function in this illustration. Likewise, in FIG. 9, computing device 902 ('first device' in figure) may interface with computing device 904 ('second device' in figure), which may, for example, also comprise features of a client computing device and/or a server computing device, in an embodiment. Processor (e.g., processing device) 920 and memory 922, which may comprise primary memory 924 and secondary memory 926, may communicate by way of a communication bus 915, for example. The term "computing device," in the context of the present patent application, refers to a system and/or a device, such as a computing apparatus, that includes a capability to process (e.g., perform computations) and/or store digital content, such as electronic files, electronic documents, parameters, measurements, text, images, video, audio, etc. in the form of signals and/or states. Thus, a computing device, in the context of the present patent application, may comprise hardware, software, firmware, or any combination thereof (other than software per se). Computing device 904, as depicted in FIG. 9, is merely one example, and claimed subject matter is not limited in scope to this particular example.

As mentioned, for one or more embodiments, a computing device may comprise, for example, any of a wide range of digital electronic devices, including, but not limited to, desktop and/or notebook computers, high-definition televisions, digital versatile disc (DVD) and/or other optical disc players and/or recorders, game consoles, satellite television receivers, cellular telephones, tablet devices, wearable devices, personal digital assistants, mobile audio and/or video playback and/or recording devices, or any combination of the foregoing. Further, unless specifically stated otherwise, a process as described, such as with reference to flow diagrams and/or otherwise, may also be executed and/or affected, in whole or in part, by a computing device and/or a network device. A device, such as a computing device and/or network device, may vary in terms of capabilities and/or features. Claimed subject matter is intended to cover a wide range of potential variations. For example, a device may include a numeric keypad and/or other display of limited functionality, such as a monochrome liquid crystal display (LCD) for displaying text, for example. In contrast, however, as another example, a web-enabled device may include a physical and/or a virtual keyboard, mass storage, one or more accelerometers, one or more gyroscopes, global positioning system (GPS) and/or other location-identifying type capability, and/or a display with a higher degree of functionality, such as a touch-sensitive color 2D or 3D display, for example.

As suggested previously, communications between a computing device and/or a network device and a wireless network may be in accordance with known and/or to be developed network protocols including, for example, global system for mobile communications (GSM), enhanced data rate for GSM evolution (EDGE), 802.11b/g/n/h, etc., and/or worldwide interoperability for microwave access (WiMAX). A computing device and/or a networking device may also have a subscriber identity module (SIM) card, which, for example, may comprise a detachable or embedded smart card that is able to store subscription content of a user, and/or is also able to store a contact list. A user may own the computing device and/or network device or may otherwise be a user, such as a primary user, for example. A device may be assigned an address by a wireless network operator, a wired network operator, and/or an Internet Service Provider (ISP). For example, an address may comprise a domestic or international telephone number, an Internet Protocol (IP) address, and/or one or more other identifiers. In other embodiments, a computing and/or communications network may be embodied as a wired network, wireless network, or any combinations thereof.

A computing and/or network device may include and/or may execute a variety of now known and/or to be developed operating systems, derivatives and/or versions thereof, including computer operating systems, such as Windows, iOS, Linux, a mobile operating system, such as iOS, Android, Windows Mobile, and/or the like. A computing device and/or network device may include and/or may execute a variety of possible applications, such as a client software application enabling communication with other devices. For example, one or more messages (e.g., content) may be communicated, such as via one or more protocols, now known and/or later to be developed, suitable for communication of email, short message service (SMS), and/or multimedia message service (MMS), including via a network, such as a social network, formed at least in part by a portion of a computing and/or communications network, including, but not limited to, Facebook, LinkedIn, Twitter, Flickr, and/or Google+, to provide only a few examples. A computing and/or network device may also include executable computer instructions to process and/or communicate digital content, such as, for example, textual content, digital multimedia content, and/or the like. A computing and/or network device may also include executable computer instructions to perform a variety of possible tasks, such as browsing, searching, playing various forms of digital content, including locally stored and/or streamed video, and/or games such as, but not limited to, fantasy sports leagues. The foregoing is provided merely to illustrate that claimed subject matter is intended to include a wide range of possible features and/or capabilities.

In FIG. 9, computing device 902 may provide one or more sources of executable computer instructions in the form physical states and/or signals (e.g., stored in memory states), for example. Computing device 902 may communicate with computing device 904 by way of a network connection, such as via network 908, for example. As previously mentioned, a connection, while physical, may not necessarily be tangible. Although computing device 904 of FIG. 9 shows various tangible, physical components, claimed subject matter is not limited to a computing devices having only these tangible components as other implementations and/or embodiments may include alternative arrangements that may comprise additional tangible components or fewer tangible components, for example, that function differently while achieving similar results. Rather, examples are provided merely as illustrations. It is not intended that claimed subject matter be limited in scope to illustrative examples.

Memory 922 may comprise any non-transitory storage mechanism. Memory 922 may comprise, for example, primary memory 924 and secondary memory 926, additional memory circuits, mechanisms, or combinations thereof may be used. Memory 922 may comprise, for example, random access memory, read only memory, etc., such as in the form of one or more storage devices and/or systems, such as, for example, a disk drive including an optical disc drive, a tape drive, a solid-state memory drive, etc., just to name a few examples.

Memory 922 may be utilized to store a program of executable computer instructions. For example, processor 920 may fetch executable instructions from memory and proceed to execute the fetched instructions. Memory 922 may also comprise a memory controller for accessing device readable-medium 940 that may carry and/or make accessible digital content, which may include code, and/or instructions, for example, executable by processor 920 and/or some other device, such as a controller, as one example, capable of executing computer instructions, for example. Under direction of processor 920, a non-transitory memory, such as memory cells storing physical states (e.g., memory states), comprising, for example, a program of executable computer instructions, may be executed by processor 920 and able to generate signals to be communicated via a network, for example, as previously described. Generated signals may also be stored in memory, also previously suggested.

Memory 922 may store electronic files and/or electronic documents, such as relating to one or more users, and may also comprise a computer-readable medium that may carry and/or make accessible content, including code and/or instructions, for example, executable by processor 920 and/or some other device, such as a controller, as one example, capable of executing computer instructions, for example. As previously mentioned, the term electronic file and/or the term electronic document are used throughout this document to refer to a set of stored memory states and/or a set of physical signals associated in a manner so as to thereby form an electronic file and/or an electronic document. That is, it is not meant to implicitly reference a particular syntax, format and/or approach used, for example, with respect to a set of associated memory states and/or a set of associated physical signals. It is further noted an association of memory states, for example, may be in a logical sense and not necessarily in a tangible, physical sense. Thus, although signal and/or state components of an electronic file and/or electronic document, are to be associated logically, storage thereof, for example, may reside in one or more different places in a tangible, physical memory, in an embodiment.

Algorithmic descriptions and/or symbolic representations are examples of techniques used by those of ordinary skill in the signal processing and/or related arts to convey the substance of their work to others skilled in the art. An algorithm is, in the context of the present patent application, and generally, is considered to be a self-consistent sequence of operations and/or similar signal processing leading to a desired result. In the context of the present patent application, operations and/or processing involve physical manipulation of physical quantities. Typically, although not necessarily, such quantities may take the form of electrical and/or magnetic signals and/or states capable of being stored, transferred, combined, compared, processed and/or otherwise manipulated, for example, as electronic signals and/or states making up components of various forms of digital content, such as signal measurements, text, images, video, audio, etc.

It has proven convenient at times, principally for reasons of common usage, to refer to such physical signals and/or physical states as bits, values, elements, parameters, symbols, characters, terms, numbers, numerals, measurements, content and/or the like. It should be understood, however, that all of these and/or similar terms are to be associated with appropriate physical quantities and are merely convenient labels. Unless specifically stated otherwise, as apparent from the preceding discussion, it is appreciated that throughout this specification discussions utilizing terms such as "processing," "computing," "calculating," "determining", "establishing", "obtaining", "identifying", "selecting", "generating", and/or the like may refer to actions and/or processes of a specific apparatus, such as a special purpose computer and/or a similar special purpose computing and/or network device. In the context of this specification, therefore, a special purpose computer and/or a similar special purpose computing and/or network device is capable of processing, manipulating and/or transforming signals and/or states, typically in the form of physical electronic and/or magnetic quantities, within memories, registers, and/or other storage devices, processing devices, and/or display devices of the special purpose computer and/or similar special purpose computing and/or network device. In the context of this particular patent application, as mentioned, the term "specific apparatus" therefore includes a general purpose computing and/or network device, such as a general purpose computer, once it is programmed to perform particular functions, such as pursuant to program software instructions.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and/or storage of charge or a release of stored charge. Likewise, in other memory devices, a change of state may comprise a physical change, such as a transformation in magnetic orientation. Likewise, a physical change may comprise a transformation in molecular structure, such as from crystalline form to amorphous form or vice-versa. In still other memory devices, a change in physical state may involve quantum mechanical phenomena, such as, superposition, entanglement, and/or the like, which may involve quantum bits (qubits), for example. The foregoing is not intended to be an exhaustive list of all examples in which a change in state from a binary one to a binary zero or vice-versa in a memory device may comprise a transformation, such as a physical, but non-transitory, transformation. Rather, the foregoing is intended as illustrative examples.

Referring again to FIG. 9, processor 920 may comprise one or more circuits, such as digital circuits, to perform at least a portion of a computing procedure and/or process. By way of example, but not limitation, processor 920 may comprise one or more processors, such as controllers, microprocessors, microcontrollers, application specific integrated circuits, digital signal processors, programmable logic devices, field programmable gate arrays, the like, or any combination thereof. In various implementations and/or embodiments, processor 920 may perform signal processing, typically substantially in accordance with fetched executable computer instructions, such as to manipulate signals and/or states, to construct signals and/or states, etc., with signals and/or states generated in such a manner to be communicated and/or stored in memory, for example.

FIG. 9 also illustrates device 904 as including a component 932 operable with input/output devices, for example, so that signals and/or states may be appropriately communicated between devices, such as device 904 and an input device and/or device 904 and an output device. A user may make use of an input device, such as a computer mouse, stylus, track ball, keyboard, and/or any other similar device capable of receiving user actions and/or motions as input signals. Likewise, a user may make use of an output device, such as a display, a printer, etc., and/or any other device capable of providing signals and/or generating stimuli for a user, such as visual stimuli, audio stimuli and/or other similar stimuli.

In the preceding description, various aspects of claimed subject matter have been described. For purposes of explanation, specifics, such as amounts, systems and/or configurations, as examples, were set forth. In other instances, well-known features were omitted and/or simplified so as not to obscure claimed subject matter. While certain features have been illustrated and/or described herein, many modifications, substitutions, changes and/or equivalents will now occur to those skilled in the art. It is, therefore, to be understood that the appended claims are intended to cover all modifications and/or changes as fall within claimed subject matter.

What is claimed is:

1. An apparatus, comprising:
   at least one processor to obtain signals and/or states representative of behavioral profile content for a particular user, the behavioral profile content to include a plurality of parameters representative at least in part of a current behavioral state and/or biological state of the particular user; and
   at least one memory to store the signals and/or states representative of the behavioral profile content;
   wherein the at least one processor to execute one or more operations to determine one or more patterns, relationships or correlations, or any combination thereof, between the behavioral profile content and one or more parameters representative of interactive game content to be currently consumed by the particular user and to generate one or more recommendations directed to improvement of a future biological state of the particular user with respect to hunger or dehydration, or a combination thereof; and wherein the at least one processor to generate the one or more recommendations directed to improvement of the future biological state of the particular user with respect to hunger or dehydration, or the combination thereof, to include tailoring signage within the interactive game content to be currently consumed by the particular user to induce the particular user to take action to address hunger or dehydration, or the combination thereof, the one or more recommendations to be communicated to the particular user via the content to be currently consumed by the particular user.

2. The apparatus of claim 1, wherein the at least one processor to obtain the behavioral profile content for the particular user at least in part from a behavioral content processor dedicated at least in part to generation of behavioral profile content, wherein the behavioral content processor to process signals and/or states obtained from one or more sensors to generate one or more specified sets of parameters representative at least in part of current behavioral states and/or biological states of one or more users, wherein the behavioral profile content is available to be utilized by a plurality of devices, systems or processes for one or more of a plurality of applications and/or purposes.

3. The apparatus of claim 1, wherein the at least one processor to repetitively obtain updated behavioral profile content.

4. The apparatus of claim 1, wherein the behavioral profile content for the particular user to comprise a plurality of parameters representative of focal point, excitement, anger, fear, fatigue, dehydration or focus/distraction, or any combination thereof.

5. The apparatus of claim 1, wherein the behavioral profile content for the particular user to include one or more parameters representative of pre-breakthrough, silent like, regret/error acknowledgment, hunger, sloppiness/precision, empathy, confusion or social engagement level, or any combination thereof.

6. The apparatus of claim 1, wherein the at least one processor to generate the one or more recommendations further based at least in part on one or more parameters representative of: general sentiment; location; time of day; or presence, identity, or state of an external individual other than the particular user; or a combination thereof.

7. The apparatus of claim 1, wherein the one or more operations to comprise one or more machine learning operations.

8. The apparatus of claim 1, wherein the at least one processor to generate the one or more recommendations directed to the improvement of the future biological state of the particular user with respect to hunger or dehydration, or the combination thereof, further based at least in part on one or more parameters representative of a presence and/or identity of an external individual other than the particular user.

9. The apparatus of claim 1, wherein the at least one processor to execute the one or more operations to identify a silent like for the particular user.

10. A method, comprising:
obtaining, via at least one processor of at least one computing device, one or more signals and/or states representative of behavioral profile content for a particular user, wherein the behavioral profile content includes a plurality of parameters representative at least in part of a current behavioral state and/or biological state of the particular user;

generating one or more recommendations directed to improvement of a future biological state of the particular user with respect to hunger or dehydration, or a combination thereof, at least in part via the at least one processor executing one or more operations to determine one or more patterns, relationships and/or correlations, or any combination thereof, between the behavioral profile content and one or more parameters representative of interactive game content currently being consumed by the particular user, wherein the generating the one or more recommendations directed to improvement of the future biological state of the particular user with respect to hunger or dehydration, or the combination thereof, includes tailoring signage within the interactive game content currently being consumed by the particular user to induce the particular user to take action to address hunger or dehydration, or the combination thereof; and communicating the one or more recommendations to the particular user via the content currently being consumed by the particular user.

11. The method of claim 10, wherein the obtaining the one or more signals and/or states representative of the behavioral profile content comprises repetitively obtaining updated behavioral profile content.

12. The method of claim 10, wherein the behavioral profile content for the particular user comprises a plurality of parameters representative of focal point, excitement, anger, fear, fatigue, dehydration, focus/distraction, pre-breakthrough, silent like, regret/error acknowledgment, probable focal point, hunger, sloppiness/precision, empathy, confusion or social engagement level, or any combination thereof.

13. The method of claim 10, wherein the generating the one or more recommendations directed to the improvement of the future biological state of the particular user further comprises generating the one or more recommendations based at least in part on one or more parameters representative of: general sentiment; location; time of day; or presence, identity or state of an external individual other than the particular user, or a combination thereof.

14. The method of claim 10, wherein the executing the one or more operations comprises executing, via the at least one processor, one or more machine learning operations.

15. The method of claim 10, wherein the executing the one or more operations includes executing one or more operations to identify a silent like for the particular user.

16. The method of claim 10, wherein generating the one or more recommendations directed to the improvement of the future biological state of the particular user with respect to hunger or dehydration, or the combination thereof, comprises tailoring the interactive game content currently being consumed by the particular user to induce the particular user to take action to address hunger or dehydration, or the combination thereof.

17. The method of claim 16, wherein the tailoring the interactive game content currently being consumed by the particular user to induce the particular user to take action to address hunger or dehydration, of the combination thereof, includes generating suggestive content within the interactive game content.

18. The method of claim 10, wherein the interactive game content currently being consumed by the particular user comprises visual content.

* * * * *